(12) United States Patent
Modlin et al.

(10) Patent No.: US 6,517,839 B1
(45) Date of Patent: Feb. 11, 2003

(54) METHODS FOR INDUCING INTERLEUKIN-12 AND A TYPE1/TH1 T-CELL RESPONSE

(75) Inventors: Robert L. Modlin, Sherman Oaks, CA (US); Daniel H. Libraty, Bangkok (TH)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/118,426

(22) Filed: Jul. 17, 1998

Related U.S. Application Data

(60) Provisional application No. 60/052,970, filed on Jul. 18, 1997.

(51) Int. Cl.[7] ............................................... A61K 39/02

(52) U.S. Cl. .............................. 424/190.1; 424/184.1; 424/185.1; 424/193.1; 424/194.1

(58) Field of Search ........................... 424/184.1, 190.1, 424/185.1, 193.1, 194.1

(56) References Cited

FOREIGN PATENT DOCUMENTS

| WO | WO 93/07897 | 4/1993 |
|---|---|---|
| WO | WO 95/29239 | 11/1995 |

OTHER PUBLICATIONS

Merrifield, R.B., "Solid Phase Peptide Synthesis. I. The Synthesis of a Tetrapeptide," *Journal of the American Chemical Society*, 1963, 85:2149–54. (Exhibit 4).

Mosmann, Timothy R. et al., "Two Types of Murine Helper T Cell Clone I. Definition According to Profiles of Lymphokine Activities and Secreted Proteins," *The Journal of Immunology*, Apr. 1, 1986, 136:2348–57. (Exhibit 5).

Hoffmann, Petra et al., "Stimulation of Human and Murine Adherent Cells by Bacterial Lipoprotein and Synthetic Lipopeptide Analogues," *Immunobiology*, 1988, 177:158–70. (Exhibit 6).

Scott, Phillip et al., "Immunoregulation of Cutaneous Leishmaniasis T Cell Lines that Transfer Protective Immunity or Exacerbation Belong to Different T Helper Subsets and Respond to Distinct Parasite Antigens," *The Journal of Experimental Medicine*, Nov. 1, 1988, 168:1675–84. (Exhibit 7).

Heinzel, Frederick P. et al., "Reciprocal Expression of Interferon γ or Interleukin 4 During the Resolution or Progression of Murine Leishmaniasis Evidence for Expansion of Distinct Helper T Cell Subsets," *The Journal of Experimental Medicine*, Jan. 1, 1989, 169:59–72. (Exhibit 8).

Ashbridge, Kevin R. et al., "Nucleotide Sequence of the 19 kDa Antigen Gene From *Mycobacterium tuberculosis*," *Nucleic Acids Research*, 1989, 17:1249. (Exhibit 9).

Liew, Foo Y. et al., "Macrophage Activation by Interferon–γ from Host–Protective T Cells is Inhibited by Interleukin (IL)3 and IL4 Produced by Disease–Promoting T Cells in Leishmaniasis," *European Journal of Immunology*, 1989, 19:1227–32 (Exhibit 10).

Sadick, Michael D. et al., "Cure of Murine Leishmaniasis with Anti–Interleukin 4 Monoclonal Antibody Evidence for a T Cell–dependent, Interferon γ–independent Mechanism," *The Journal of Experimental Medicine*, Jan. 1, 1990, 171:115–27. (Exhibit 11).

Hauschildt, Sunna et al., "Activation of Bone Marrow–Deprived Mouse Macrophages by Bacterial Lipopeptide: Cytokine Production Phagocytosis and Ia Expression," *European Journal of Immunology*, 1990, 20:63–8. (Exhibit 12).

Yamamura, Masahiro et al., "Defining Protective Responses to Pathogens: Cytokine Profiles in Leprosy Lesions," Oct. 11, 1991, 154:277–9. (Exhibit 13).

Salgame, Padmini et al., "Differing Lymphokine Profiles of Functional Subsets of Human CD4 and CD8 T Cell Clones," *Science*, Oct. 11, 1991, 254:279–82. (Exhibit 14).

Romagnani, Sergio, "Induction of TH1 and TH2 Responses: A Key Role for The 'Natural' Immune Response?" *Immunology Today*, 1992, 13:379–81. (Exhibit 15).

Bloom, Barry R. and Murray, Christopher J.L., "Tuberculosis: Commentary of A Reemergent Killer," *Science*, Aug. 21, 1992, 257:1055–64. (Exhibit 16).

D'Andrea, Annalisa et al., "Production of Natural Killer Cell Stimulatory Factor (Interleukin 12) by Peripheral Blood Mononuclear Cells," *The Journal of Expreimental Medicine*, Nov. 1992, 176:1387–98. (Exhibit 17).

Hsieh, Chyi–Song et al., "Development of Th1 CD4[+] T Cells Through IL–12 Produced by Listeria–Induced Macrophages," *Science*, Apr. 23, 1993, 260:547–9. (Exhibit 18).

Heinzel, F.P. et al., "Recombinant Interleukin 12 Cures Mice Infected with *Leishmania major*," *Journal of Experimental Medicine*, May 1993, 177:1505–9. (Exhibit 19).

Cooper, Andrea M. et al., "Disseminated Tuberculosis in Interferon γ Gene–disrupted Mice," *The Journal of Experimental Medicine*, Dec. 1993, 178:2243–7. (Exhibit 20).

(List continued on next page.)

*Primary Examiner*—Patrick J. Nolan
*Assistant Examiner*—Gerald R. Ewoldt
(74) *Attorney, Agent, or Firm*—Mandel & Adriano

(57) ABSTRACT

Methods for inducing interleukin-12 production and inducing a type 1/Th1 T cell response in a subject, thereby stimulating cell-mediated immunity for prevention or treatment of pathogen infections or treatment of a interferon (-sensitive tumor, are provided. Compounds effective in the above-described methods include a lipopeptide having an N-terminal ester- or amide-linked fatty acyl group and are administered in an amount effective to induce interleukin-12 and to induce the type 1/Th1 T-cell response. Preferably, the subject is a human patient, and the lipopeptide is an N-terminal moiety of a 19 kDa or a 38 kDa lipoprotein of *Mycobacterium tuberculosis*.

2 Claims, 10 Drawing Sheets

OTHER PUBLICATIONS

Flynn, JoAnne L. et al., "An Essential Role for Interferon γ in Resistance to *Mycobacterium tuberculosis* Infection," *The Journal of Experimental Medicine,* Dec. 1993, 178:2249–54. (Exhibit 21).

Zhang, Ming et al., "Interleukin 12 at the Site of Disease in Tuberculosis," *The Journal of Clinical Investigation,* Apr. 1994, 93:1733–9. (Exhibit 22).

Ma, Ying et al., "Outer Surface Lipoproteins of *Borrelia burgdorferi* Stimulate Nitric Oxide Production by the Cytokine–Inducible Pathway," *Infection and Immunity,* Sep. 1994, 62:3663–71. (Exhibit 23).

Gazzinelli, Ricardo T. et al., "Parasite–Induced IL–12 Stimulates Early IFN–γ Synthesis and Resistance During Acute Infection with *Toxoplasma gondii,*" *The Journal of Immunology,* Sep. 15, 1994, 153:2533–43. (Exhibit 24).

Sieling, Peter A. et al., "IL–12 Regulates T Helper Type 1 Cytokine Responses in Human Infectious Disease," *The Journal of Immunology,* Oct. 1994, 153:3639–47. (Exhibit 25).

Cooper, A. M. et al., "The Role of Interleukin–12 in Acquired Immunity to *Mycobacterium tuberculosis* Infection," *Immunology,* Mar. 1995, 84:423–32. (Exhibit 26).

Radolf, Justin D. et al., "*Treponema pallidum* and *Borrelia burgdorferi* Lipoproteins and Synthetic Lipopeptides Activate Monocytes/Macrophages," *The Journal of Immunology,* Mar. 15, 1995, 154:2866–77. (Exhibit 27).

Flynn, JoAnne L. et al., "IL–12 Increases Resistance of BALB/c Mice to *Mycobacterium tuberculosis* Infection," *The Journal of Immunology,* Sep. 1, 1995, 155:5215–24. (Exhibit 28).

Wilkinson, Victoria L. et al., "Characterization of Anti--mouse IL–12 Monoclonal Antibodies and Measurement of Mouse IL–12 by ELISA," *Journal of Immunological Methods,* 1996, 189:15–24. (Exhibit 29).

Berman, Jeffrey S. et al., "Chemotactic Activity of Mycobacterial Lipoarabinomannans for Human Blood T Lymphocytes In Vitro," *The Journal of Immunlogy,* May 15, 1996, 156:3828–35. (Exhibit 30).

Kumar et al., 1990, Proc. Acad. Sci. USA, 87:1337–1341.*

Finkelman et al., 1994, J. Exp. Med., 179:1563–1572.*

Germann et al., 1995, Immunology, 7:1649–1657.*

Jeannin et al. J. Immunol. 156:3159–3165, 1996.*

* cited by examiner

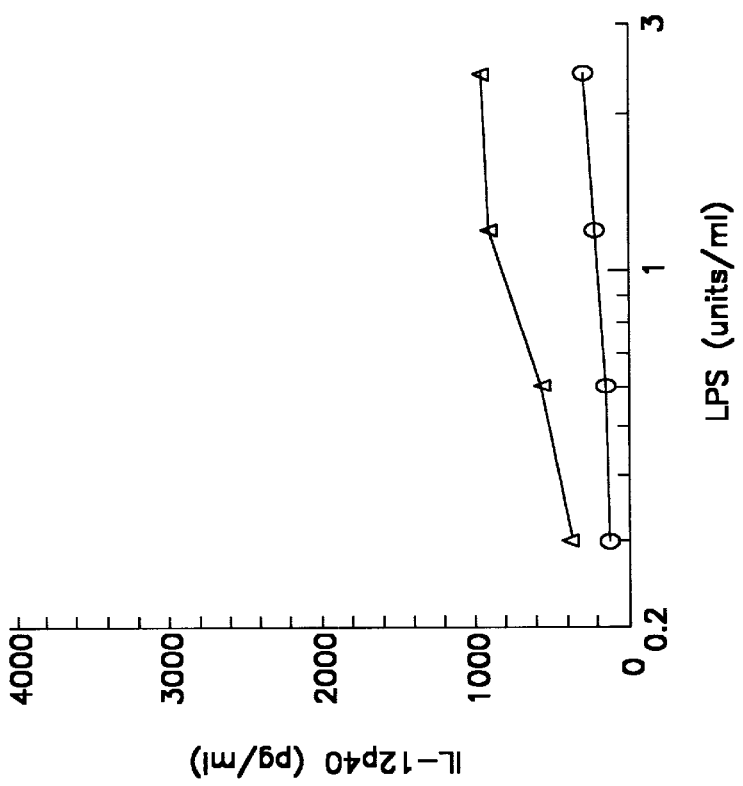
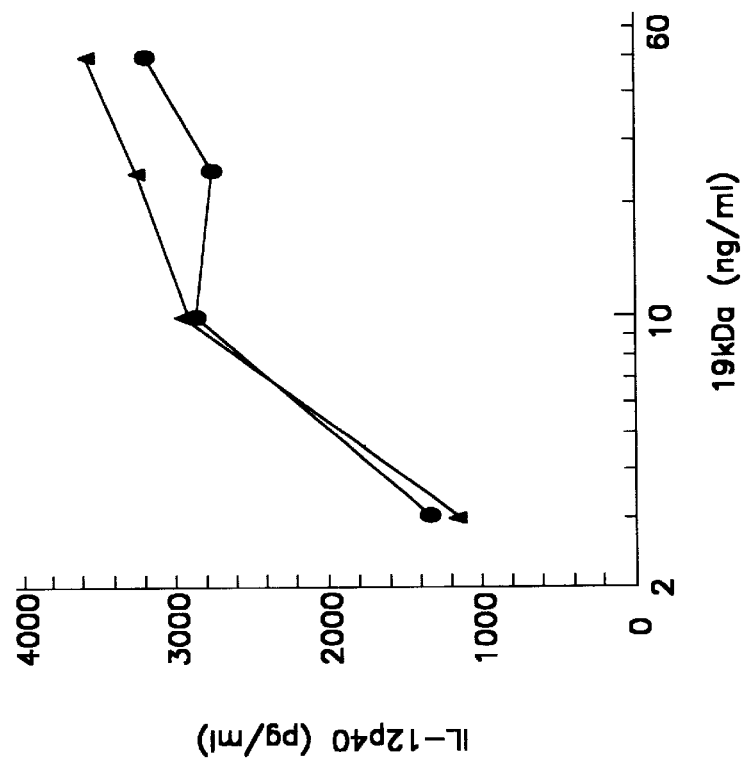
FIG. 9A
FIG. 9B

METHODS FOR INDUCING INTERLEUKIN-12 AND A TYPE1/TH1 T-CELL RESPONSE

This application claims priority to U.S. Provisional Application Serial No. 60/052,970, filed Jul. 18, 1997, the contents of which are incorporated by reference into the present application.

FIELD OF THE INVENTION

The present invention relates generally to the fields of medical microbiology and immunology. More particularly, the invention provides methods for inducing the production of interleukin-12 in peripheral blood mononuclear cells and, thereby, inducing a type 1/Th1 T cell immune response that is central to an effective cell-mediated immune response to intracellular pathogens or interferon γ-sensitive tumors.

BACKGROUND OF THE INVENTION

Infection with the intracellular pathogen *Mycobacterium tuberculosis* (*M. tuberculosis*) continues to produce great morbidity and mortality throughout the world with 8 million new cases of tuberculosis and 3 million deaths occurring annually. Such creates an urgency to understand mechanisms of cell-mediated immunity (CMI) to the infection (Bloom and Murray, *Science* 257: 1055–1064, 1992). The spectrum of clinical outcomes after infection with *M. tuberculosis* is determined largely by the interaction of T-cells and monocyte/macrophages. Two functionally distinct subsets of T-cells modulate the outcome of such intracellular infections (Mosmann et al., *J. Immunol* 136:2348–2357, 1986). In human infectious disease, Type 1 T-cells that produce interleukin-2 (IL-2) and interferon γ (IFN-γ) activate macrophages to kill or inhibit the growth of pathogens, resulting in mild or self-curing disease (Yamamura et al., *Science* 254:277–279, 1991; Salgame et al., *Science* 254:279–282, 1991). In contrast, type 2 T-cells which produce interleukins-4, -5, and -10 (IL-4, IL-5, IL-10) augment humoral responses (circulating antibody responses) and inhibit CMI, resulting in fulminant disease. The differentiation of naive T-cells into producing either type 1 or type 2 cytokine profiles is shaped by the cytokine milieu produced by the surrounding monocytes and macrophages. In particular, interleukin-12 (IL-12) is a key bridge between the innate immune response of monocyte/macrophages and the adaptive immune response of type 1 T-cells (Romagnani, S., *Immunol Today* 13:379–381, 1992).

IL-12, a cytokine or hormone-like substance, is produced by activated monocytes as a heterodimeric protein composed of p35 and p40 subunits. The p40 subunit is inducible and is considered to be the regulatory component for IL-12 expression (D'Andrea et al., *J Exp Med* 176:1387–1398, 1992). IL-12 production in response to microbial pathogens leads to activation of natural killer (NK) cells and T-cells with ensuing production of IFN-γ. In the presence of high IFN-γ and low IL-4, there is subsequent development of a type 1 T-cell cytokine response and vigorous CMI (Hsieh et al., *Science* 260:547–549, 1993; Gazzinelli et al., *J Immunol* 153:2533–2543, 1994; Heinzel et al., *J Exp Med* 177:1505–1509, 1993).

In animal models of infection due to intracellular pathogens, the production of IL-12 is important in the generation of protective, Th1-mediated, immunity (Scott et al., *J Exp Med* 168:1675–1684, 1988; Heinzel et al.; *J Exp Med* 169:591989; Liew et al., *Eur J Immunol* 19:1227–1232, 1989; Sadick et al., *J Exp Med* 171:115–127, 1990). For example, in mycobacterial infection, IL-12 production at the site of disease is a prominent characteristic of the resistant phenotype or self-limited disease. In tuberculosis, IL-12 has been found in the pleural fluid of patients with tuberculous pleuritis; and, anti-IL-12 antibodies partially inhibit the proliferative response of the pleural fluid lymphocytes to *M. tuberculosis* (Zhang et al., *J Clin Invest* 93:1733–1739, 1994). In leprosy, IL-12 induces the expansion of mycobacteria-reactive T-cells which produce IFN-γ, but has little effect on T-cells which produce IL-4 (Sieling et al., *J Immunol* 153:3639–3647, 1994). Further, in a murine model, exogenous administration of IL-12 increases the resistance of mice to *M. tuberculosis* infection via the IFN-γ pathway (Flynn et al., *J Immunol* 155:2515–2524, 1995; Cooper et al., *Immunology* 84:423–432, 1995). In addition, production of IFN-γ is required for immunity to mycobacterial infection (Flynn et al., *J Exp Med* 178:2249–2254, 1993; Cooper et al., *J Exp Med* 178:2243–2247, 1993).

A number of prokaryotic lipoproteins reportedly are potent macrophage stimulators. Examples include the TraT and Braun lipoproteins of *E. coli*, the outer membrane proteins of *Treponema pallidum* and *Borrelia burgdorferi*, and a lipoprotein of *Mycoplasma fermentans*. The *B. burgdorferi* OspA antigen and the 47 kDa antigen of *T. pallidum* have been reported to induce IL-12 mRNA (Ma et al., *Infect Immun* 62:3663, 1994; Radolf et al., *J Immunol* 154:2866, 1995).

The nature of an immune response reflects the profile of antigen-specific lymphocytes that are stimulated by the immunization. T cells consist of subpopulations that may be stimulated by different types of antigens and perform different effector functions. For example, in viral infections, viral antigens are synthesized in infected cells and presented in association with class I major histocompatibility complex (MHC) molecules leading to stimulation of CD8+, class I MHC-restricted cytotoxic lymphocytes. In contrast, extracellular microbial antigens are endocytosed by antigen presenting cells, processed, and presented in association with class II MHC molecules. This activates CD4+, class II MHC-restricted helper T cells, leading to antibody production and macrophage activation but relatively inefficient development of cytotoxic lymphocytes.

IL-12 promotes the development of Th1 cells, and microbes that stimulate macrophages to produce IL-12 or natural killer (NK) cells to produce IFN-γ induce Th1-dominated responses. A type 1/Th1 T-cell response is where CD4+ helper Th1 cells secrete interleukin-2 and interferon-γ which activates macrophages and are the principal effectors of cell-mediated immunity against intracellular microbes and of delayed type hypersensitivity. The antibody isotypes stimulated by Th1 cells are effective at activating complement and opsonizing antigens for phagocytosis. Therefore, Th1 cells trigger phagocyte-mediated host defense.

IL-4 stimulates differentiation of CD4+ T cells toward Th2 cells, and parasites, in general, induce early IL-4 production. Th2 cells also produce interleukin-4, which stimulates IgE antibody production, IL-5, IL-10 and IL-3, which together with IL-4 suppress cell-mediated immunity. Therefore, the Th2 subset of T cells is mainly responsible for phagocyte-independent host defense, e.g., against parasites; which is mediated by IgE and for allergic reactions, which are due to IgE-dependent activation of mast cells and basophils.

Protective immunity induced by vaccination is dependent on the capacity of the vaccine to elicit the appropriate immune response to either resist, control, or eliminate the pathogen. Adjuvants are substances capable of increasing the immunogenicity of antigens; such substances include aluminum salts, bacterial endotoxins, bacillus Calmette-GuJrin (BCG), or *Bordetella pertussis*, for example. Adjuvants stimulate the immune response by combining with antigen and forming an aggregate; this aggregate acts as a depot for prolonged antigen stimulation. In experiments with animals, the most frequently used adjuvants are Freund's complete and incomplete adjuvants, which include water and oil emulsions with or without heat-killed *Mycobacterium tuberculosis*. The use of bacterial adjuvants to augment systemic immune responses in a nonspecific way is not without possible dangers. Repeated inoculation with live BCG organisms has caused systemic mycobacterial infections in several patients. To avoid this complication, other bacterial adjuvants, such as killed preparations of *Corynebacterium parvum* have been tested, and attempts have been made to extract the immunopotentiating component from BCG. In addition to prolonging antigen stimulation, adjuvants may also stimulate the immune response by influencing the cytokine milieu; activity and recruiting specific cell types, etc.

Responding to the need for identification of the active component of these adjuvants to solve such problems, the present inventors provide herein the characterization of mycobactenral lipoproteins that induce IL-12 production and that are useful in the development of new vaccine and therapeutic strategies.

SUMMARY OF THE INVENTION

The present invention seeks to overcome these and other drawbacks inherent in the prior art by providing methods for inducing interleukin-12 production and inducing a type 1/Th1 T cell response, thereby stimulating cell-mediated immunity for prevention or treatment of pathogen infections or treatment of an interferon γ-sensitive tumor. The methods of the present invention are useful, by way of example, where IL-12-inducible peripheral blood mononuclear cells are in need of inducing to produce IL-12; in vivo where a subject, preferably a human patient, is in need of IL-12 induction to enhance the type 1/Th1 T cell response for enhanced cell-mediated immunity; and ex vivo where body fluids, such as blood or bone marrow, may be removed temporarily from a body and treated with compositions of the present invention for inducing IL-12 with resultant enhanced cell-mediated immunity.

Enhanced IL-12 production causes in vivo a type 1/Th1 T cell response which is required for cell-mediated immunity necessary in treatment or prevention of infections by microbial pathogens, intracellular or extracellular, as well as tumors that are interferon γ-sensitive.

One aspect of the invention provides a method of inducing a type 1/Th1 T-cell response in a subject. In one embodiment, the-method comprises administering to a subject a lipopeptide having an N-terminal ester- or amide-linked fatty acyl group in an amount effective to induce a type 1/Th1 T-cell response. A further embodiment is a method of inducing interleukin-12 in a subject comprising administering to the subject said lipopeptide in an amount effective to induce interleukin-12. One of skill in the art in light of the present disclosure can see that IL-12 induction is broader than the specific induction of cytotoxic T-cells. EP 0431327 reports the specific induction of cytotoxic T cells. The present invention proposes a conjugate compound that includes a consensus lipoprotein sequence plus an N-terminal portion of the *M. tuberculosis* 19 kDa antigen plus the protein or peptide of interest. This compound is post-transtationally modified in the appropriate manner to have activity (e.g., acylation and/or glycosylation). This conjugate compound is designed to induce a profound IL-12 release and a type 1 cell-mediated response; and to induce a specific pattern of NK activity, T-helper as well as T-cell cytotoxic responses.

The presently disclosed invention may be used in conjunction with an in vitro cell or cell culture of peripheral blood mononuclear cells having the capacity to produce IL-12; or with an animal having a functional immune system, especially a human patient in need of stimulation of the type 1/Th1 immune response. Such constitute definitions of a subject to be employed with the present inventive methods. The animal may be in need of a cell-mediated immune response to a pathogen, in particular, to the pathogen *M. tuberculosis*; or in need of a cell-mediated enhanced natural immunity to an interferon γ-sensitive tumor.

A peripheral blood mononuclear cell having the capacity to produce IL-12 is a mononuclear cell having a gene or part of a gene that encodes IL-12, and the regulatory genetic make-up and cellular machinery sufficient to respond to a lipopeptide of the present invention to induce the gene to produce messenger RNA, as well as cellular machinery sufficient to provide for the messenger RNA to be translated into the protein IL-12. A peripheral blood mononuclear cell includes a macrophage, monocyte, adherent cell, cell lines thereof, or the like.

A lipopeptide having an N-terminal ester- or amide-linked fatty acyl group has the capacity to induce IL-12 production when brought in contact with an IL-12-inducible PBMC. Capacity to induce IL-12 production means that upon exposure to the lipopeptide, the subject is stimulated to synthesize and produce the cytokine IL-12. An amount effective to induce the type 1/Th1 T-cell response means that the lipopeptide is administered in sufficient quantity so that interleukin-12 is produced which, in turn, activates T cells to produce interferon γ which, in turn, activates cell-mediated immunity.

A method of protecting a subject against infection by *M. tuberculosis* by inducing a type 1/Th1 T cell response and a method for treating a human patient having a condition responsive to a type 1/Th1 T cell immune response are farther aspects of the invention. Each method comprises administering to the subject a lipopeptide having an N-terminal ester- or amide-linked fatty acyl group in an amount effective to induce the type 1/Th1 T-cell response. Protecting a subject means prevention by providing the lipopeptide in a vaccine prior to exposure to a pathogen, for example, or means treatment of a subject already having an infection or an interferon γ-sensitive tumor, for example.

A particular advantage of the present invention is the identification of the active agents of the mycobacterium cell wall having activity for inducing IL-12. Heretofore, it was necessary to administer the complete complement of normal or heat-killed cell wall components to induce an immune response. The present inventors' showing that the 19 kDa lipoprotein of *M. tuberculosis* is the active agent for inducing IL-12 means that the active agents or active portions thereof are useful for any condition benefiting from administration of IL-12. Other advantages include the ability to stimulate IL-12 release by compounds not usually associated with type 1 T-cell response, or to switch a predominant type 2 response to a type 1 response using the proposed invention.

The present invention contributes towards the development of a new class of vaccines against deadly microbial pathogens by providing molecules and mechanisms that generate effective immunity. IL-12 has been identified as one such molecule that can serve as an adjuvant in vaccination against intracellular pathogens. However, the utility of recombinant IL-12 as an adjuvant in humans is at present unclear. The present invention shows that lipopeptides, especially mycobacterial lipopeptides, may present a more natural approach to the induction of cell-mediated immunity. Lipopeptides of the present invention may be used in a new generation of protein subunit vaccines.

Following long-standing patent law convention, the terms "a" and "an" mean "one or more" when used in this application, including the claims.

ABBREVIATIONS

SDS-PAGE: Sodium dodecyl sulfate—polyacrylamide gel electrophoresis
ELISA: Enzyme-linked imnmunoadsorbent assay
PBMC: Peripheral blood mononuclear cells
LPS: Lipopolysaccharide
kDa: Kilodalton
CMI: Cell-mediated immunity
IL: Interleukin
IFN-γ: Interferon-γ

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 9A and 9B. The 19 kDa lipoprotein of *M. tuberculosis* induces IL-12 p40 production in fresh human monocytes as described in Example 6. Values are expressed as mean±SEM of duplicate determinations. 9A: 19 kDa production of IL-12 p40 in absence (▼) and presence (●) of My4 anti-CD14 Mab; 9B: LPS production IL-12 p40 in absence (Δ) and presence (○) of My4-anti-CD14 Mab.

DETAILED DESCRIPTION OF THE PREFERRED EMBODIMENTS

Figure 1:
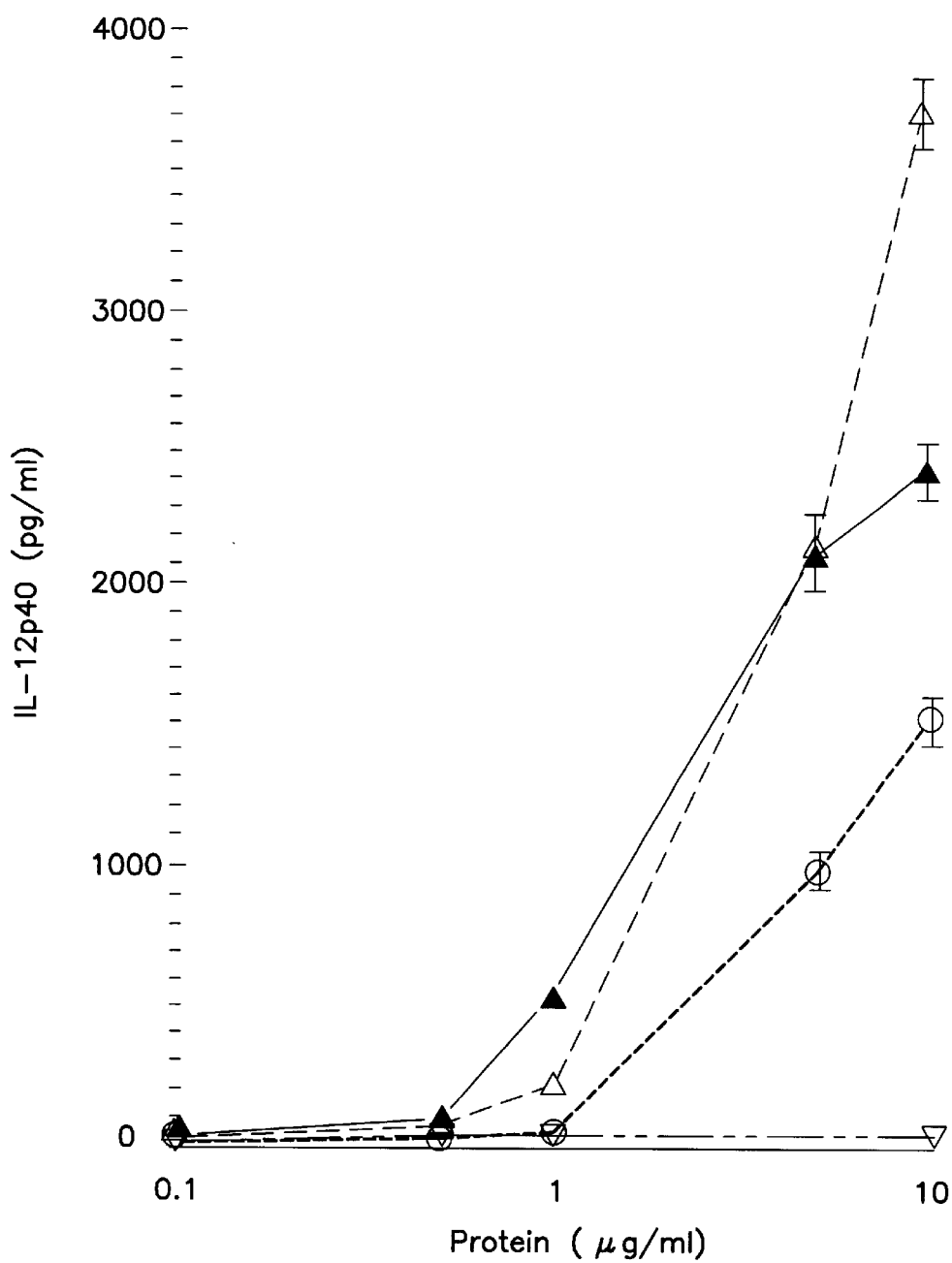
FIG. 1. The cell wall-associated subcellular fraction (SCWP, ▼) retains the majority of the *M. tuberculosis* IL-12 p40-inducing capacity seen in the mycobacterial. lysate (Δ). Data are also shown for the cytosolic and membrane fraction (○), and for manLAM (□). Values are expressed as mean±SEM of duplicate determinations. The X-axis is concentration of antigen used.

The present invention results in part from the discovery by the present inventors that the *M. tuberculosis* 19 kDa and 38 kDa lipoproteins are the major mycobacterial stimulators of IL-12 release from monocytes. The *M. tuberculosis* 19 kDa lipoprotein was found to induce IL-12 production at nanomolar concentrations. Induction of IL-12 release contributes to effective cell-mediated immunity against *M. tuberculosis* infection.

Embodiments of the invention include methods useful for stimulating and enhancing the production of IL-12 in patients as well as in isolated cells and cell cultures; the production of IL-12 is useful for activating T cells to produce interferon γ. Where interferon y concentrations are elevated and interleukin-4 concentrations are reduced, a type 1/Th1 T cell response occurs leading to cell-mediated immune responses. Cell-mediated immunity is important for fighting infection due to pathogens such as, for example, *Borrelia burgdorferi* (Lyme disease), *Treponema pallidum* (syphilis), *Listeria monocytogenes, Staphylococcus aureus, Leishmania major* (leishmaniasis), *Mycobacterium tuberculosis* (tuberculosis), *Mycobacterium leprae* (leprosy), *Chlamydia trachomatis, Toxoplasma gondii, Escherichia coli, Besnoitia jellisoni, Pseudomonas aereuginosa, Haemophilus influenza, Salmonella typhi*, Nocardia sp., *Rhodococcus equi*, Actinomyces sp., virus including HIV, *Corynebacterium parvum*; and for fighting interferon γ-sensitive tumors. WO 95/29239 is incorporated by reference herein for compounds related to *Leishmanis braziliensis* antigen reportedly useful for the stimulation and enhancement of protective immune responses and IL-12 production.

As used herein, the term "subject" or "patient" refers to an animal having an immune system, including a human. A subject may be afflicted with a disease, such as those cited or cancer, or may be normal (i.e., free of detectable disease).

The peptide portion of the lipopeptide may be as short as 2–3 amino acids or may be a full length protein. An N-terminal ester- or amide-linked fatty acyl group means that a fatty acyl group is linked in an amide linkage to an N-terminal amino acid of the peptide, or means that a fatty acyl group is directly or indirectly linked in an ester linkage to an N-terminal amino acid of the peptide. Although the nature of the fatty acid residues has little influence on the biological activity, the presence of an ester-linked acyl groups is important for activity. The absence of the ester-linked fatty acids appears to remove the macronhage stimulating properties of bacterial lipoproteins. The fatty acyl group may be myristate, palmitate, palmitoleate, stearate, oleate, hydroxystearate, linoleic, or the like. The composition of the fatty acids on the acyl grpop of the 19 kDa antigen in mycobacteria is not completely known. Palmitic acid is not likely in mycobacteria like other eubacteria. Another fatty acid that exists in *M. tuberculosis* is tuberculosteric acid. One particular lipopeptide is Xaa-Ser-Ser, Xaa-Gly-Ser, Xaa-Ser-Ser-Asn-Lys-Ser (SEQ ID NO:3), or Xaa-Gly-Ser-Lys-Pro-Pro (SEQ ID NO:7) wherein Xaa is an N-acyldiacylglycerol-cysteine residue. In some embodiments, Xaa is N-tripalmitoyl-S-glyceryl cysteine. A further embodiment of the invention is provided where the lipopeptide is a 19 kDa antigen or a 38 kDa antigen of *M. tuberculosis* having an N-terminal N-acyldiacylglycerol-cysteine residue. Further examples of lipopeptides useful in the present invention may be found in European patent, EP 0431327, incorporated by reference herein in its entirety. Further lipopeptides useful in the present invention include: Xaa-Ser-Ser-Asn-Ala (SEQ ID NO:8), Xaa-Gly-Ser-Ser-His-His (SEQ ID NO:9), Xaa-Ser-Ser-Lys-Thr-Asp (SEQ ID NO:10), Xaa-Lys-Gln-Asn-Val-Ser- (SEQ ID NO:11), Xaa-Ala-Gln-Lys-Gly-Ala (SEQ ID NO:12), Xaa-Ala-Gly (SEQ. ID NO:13), or Xaa-Ser (SEQ ID NO:14), for example.

The synthesis of the lipid derivatized amino acid Xaa as cited herein would be known to one of skill in the art in light of the present disclosure and is presented in Radolf et al., (*J Immunology* 154:2866, 1995), incorporated by reference herein. An N-acyldiacylglyceryl-cysteinyl may be represented by

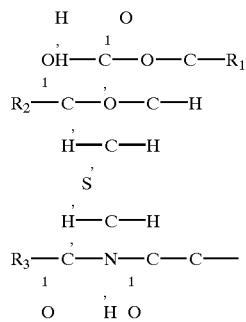

Each of $R_1$, $R_2$, and $R_3$ is a fatty acyl group.

In some embodiments, Xaa is S-(2,3-bis(palmitoyloxy)-(2RS)-propyl)-N-palmitoyl-(R)-cysteinyl (Radolf et al., *J Immunology* 154:2866, 1995, previously incorporated by reference herein):

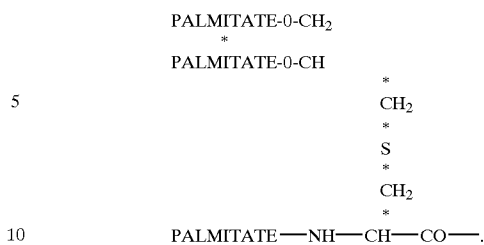

In some embodiments, the peptide portion of the lipopeptide of the present invention may have from 2–3 amino acids up to the number of amino acids in a particular full length protein. The amino-acid composition of the N-terminal region appears to determine the extent of stimulation by a lipopeptide. Peptide synthesis is also well known to one of skill in the art and the lipopeptides cited herein could be synthesized without undue experimentation (see, for example: EP 0431327; Hauschildt et al., *Eur. J. Immunol.* 20:63, 1990; Hoffmann, et al., *Immunobiol.* 177:158, 1988; each reference is incorporated by reference herein). The lipid portion of the lipopeptide and the peptide may be provided in a mixture where there is no covalent bond between the lipid and the peptide or in a conjugate where they are covalently bonded. In a mixture where there is no covalent bond between the "lipid" and "peptide" is that the lipid would actually be either a lipopeptide derived from the *M. tuberculosis* 19 kDa antigen, o the entire lipoprotein itself. Similarly, a recombinant or conjugate lipopeptide would incorporate the N-terminal lipopeptide portion of the *M. tuberculosis* 19 kDa antigen. Lipopeptides of the present invention include variants that retain the ability to stimulate production of interleukin-12 and therefore stimulate a type 1/Th1 immune response in PBMCs. Such variants include various structural forms of the primary protein. Due to the presence of ionizable amino and carboxyl groups, for example, a lipopeptide may be in the form of an acidic or basic salt, or may be in neutral form. Lipopeptides may also be modified by oxidation or reduction.

Variant lipopeptides within the scope of this invention also include lipopeptides in which the primary amino acid structure is modified by forming covalent or aggregate conjugates with other peptides or chemical moieties such as glycosyl groups, lipids, phosphate, acetyl groups and the like. Covalent derivatives may be prepared by linking particular functional groups to amino acid side chains or at the amino or carboxyl terminus.

Further variants include lipopeptides of the invention that have an amino acid sequence different from native protein sequences due of one or more deletions, insertions, substitutions or other modifications. Such variants should be substantially functionally homologous and should retain the ability to stimulate IL-12 and a type 1/Th1 immune response in PBMCS. The effect of any such modifications on the activity of a lipopeptide may be readily determined by analyzing the ability of the mutated lipopeptide to induce IL-12 or a type 1/Th1 response using, for example, an ELISA test for the presence of the p40 subunit of IL-12 as described herein.

Generally, amino acid substitutions should be made conservatively; i.e., a substitute amino acid should replace an amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr, (3) val, ile, leu, met, ala, phe; (4) lys, arg, his; and (5) phe, tyr, trp, his. Variants within the scope of this invention may also, or alternatively, contain other modifications, including the deletion or addition of amino acids, that have minimal influence on the stimulatory properties, secondary structure and hydropathic nature of the polypeptide.

A full-length protein such as the 19 kDa or the 38 kDa proteins of Mycobacterium tuberculosis may generally be obtained using a genomic or cDNA clone encoding the protein. A genomic sequence that encodes the 19 kDa protein is shown in SEQ ID NO:4, and the deduced amino acid sequence is presented in SEQ ID NO:1 (Ashbridge et al., *Nucleic Acids Research* 17(3):1249). Such clones may be isolated by screening an appropriate *Mycobacteriurn tuberculosis* expression library for clones that express the 19 kDa antigen or, alternatively, screening for clones with a hybridizable probe representing complementary sequence of DNA that encodes the 19 kDa antigen. The screening may generally be performed using methods known to those of ordinary skill in the art, such as methods described in Sambrook et al., (*Molecular Cloning: A Laboratory Manual*, Cold Spring Harbor Laboratories, Cold Spring Harbor, N.Y., 1989, incorporated herein by reference).

Lipopeptides having the ability to stimulate interleukin-12 production and a type 1/Th1 immune response in PBMCs may be identified by assaying for the ability to stimulate a type 1/Th1 response. Such assays may generally be performed by treating patient PBMCs with the lipopolypeptide and assaying for and IFNγ as described in Mosmann, et al., *J. Immunol.* 136:2348–2357, 1986.

Sequence modifications may be introduced using standard recombinant techniques or by automated synthesis of the modified peptide. For example, mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide a gene in which particular codons are altered according to the substitution, deletion, or insertion required.

The lipopeptides of the present invention, both naturally occurring and modified, may be produced by recombinant DNA methods. Such methods include inserting a DNA sequence encoding a lipopeptide into an expression vector and expressing the DNA sequence in a recombinant microbial expression system under conditions promoting expression. DNA sequences encoding the lipopeptides provided by this invention can be assembled from cDNA fragments and short oligonucleotide linkers, or from a series of oligonucleotides, to provide a synthetic gene which is capable of being inserted in a recombinant expression vector and expressed in a recombinant transcriptional unit. A lipopeptide of the present invention may also be synthesized recombinantly in a host having an acyltransferase activity that would attach a lipid portion of the lipopeptide to the peptide that is made by standard recombinant techniques. Such hosts having an acyltransferase activity include pathogenic hosts such as those listed herein. Exemplary vectors for expressing such a peptide include bacterial vectors, mycobacterial expression vectors, and yeast vectors. Bacterial expression vectors containing DNA encoding secretion signals of lipoproteins can be found in WO 93/07897, incorporated by reference herein. DNA sequences encoding the peptide portions of a lipopeptide of the present invention can be found in the literature by one of skill in the art in light of the teachings of the present specification. Select sequences are provided in Table 1.

Recombinant expression vectors contain a DNA sequence encoding a lipopeptide, operably linked to suitable transcriptional or translational regulatory elements derived from mammalian, microbial, viral or insect genes. Such regulatory elements include a transcriptional promoter, an optional operator sequence to control transcription, a sequence encoding saitable mRNA ribosomal binding sites, and sequences which control the termination of transcription and translation. An origin of replication and a selectable marker to facilitate recognition of transformants may additionally be incorporated. Expression vectors for bacterial use may comprise a selectable marker and bacterial origin of replication derived from commercially available plasmids comprising genetic elements of the well known cloning vector pBR322, for example.

DNA regions are operably linked when they are functionally related to each other. For example, a promoter is operably-linked to a coding sequence if it controls the transcription of the sequence; or a ribosome binding site is operably linked to a coding sequence if it is positioned so as to permit translation. Generally, operably-linked means contiguous and, in some cases, in reading frame. Promoters commonly used in recombinant microbial expression vectors include the $-lactamase (penicillinase) and lactose promoter system, the tryptophan (trp) promoter system, and the tac promoter.

Purified lipopeptides may be prepared by culturing suitable host/vector systems to express the recombinant translation products of the DNAs of the present invention, which are then purified from culture media or cell extracts. Concentrated media or cell extracts may be applied to a suitable purification matrix. For example, a suitable affinity matrix may comprise a counter-structure protein (i.e., a protein to which the lipopeptide binds in a specific interaction hased on stnicture) or antibody molecule bound to a suitable support. Gel filtration chromatography or affinity chromotography also provide a means of purifying a lipopeptide. High performance liquid chromatography (HPLC) may be employed for final purification steps. Microbial cells employed in expression of recombinant lipoprotein can be disrupted by any convenient method, including freeze-thaw cycling, sonication, mechanical disruption, or use of cell lysing agents.

Automated synthesis provides an alternative method for preparing lipopeptides of the present invention having fewer than about 100 amino acids, and typically fewer than about 50 amino acids. For example, the Merrifield solid phase synthesis method may be employed, in which amino acids are sequentially added to a growing amino acid chain. (Merrifield, *J. Am. Chem. Soc.* 85:2149–2146, 1963.) Equipment for automated synthesis of polypeptides is commercially available from suppliers such as Applied Biosystems, Inc. (Foster City, Calif.). The lipid portion of the lipopeptide is added in a synthetic step after the peptide portion is removed from automated synthesis.

The invention provides methods of using a lipopeptide disclosed herein for stimulating IL-12 production and a type 1/Th1 T cell response. It has been found within the present invention that the 19 kDa and 38 kDa antigens of *Mycobacterium tuberculosis* stimulate IL-12 production from PBMCs, thereby stimulating a type 1/Th1 T cell response. A type 1/Th1 T cell response is characterized by the production of the cytokines interleukin-1, interleukin-2, interleukin-12 or interferon-γ, as well as tumor necrosis factor-".

A lipopeptide of the present invention also stimulates a type 1/Th1 cytokine profile of mRNAs such as those encoding IFN-γ, IL-1, IL-2, IL-12 p40 subunit, and TNF-α, in PBMCs. No detectable IL-4 or IL-10 mRNA, indicative of a type 2/Th2 response, is present in such stimulated PBMCs.

The present invention provides methods for stimulating a type 1/Th1 T cell response in PBMCs and isolated component cells (including, but not limited to, macrophages, monocytes and dendritic cells). For stimulation of such cells, the cells may be isolated by any of a variety of techniques well known to those skilled in the art (such as Ficoll-hypaque density centrifugation), and contacted with a lipopeptide of the present invention in sufficient quantities and for a sufficient time to generate a type 1/Th1 T cell response, as described above. The cells treated according to this invention may (but need not) have been isolated from a patient afflicted with tuberculosis, or another disorder, and may be reintroduced into a patient after treatment. For cells obtained from tuberculosis-infected individuals, the immune responses generated include a type 1/Th1 immune response (which includes stimulation of IL-12 production) and the down-regulation of IL-10 expression. For cells from uninfected individuals, the immune response may be the production of IL-12.

In another embodiment, the present invention provides methods for stimulating or enhancing immune responses in patients, including humans. In one embodiment, a lipopeptide of the present invention may be used as an immunomodulating agent to enhance a cellular and/or humoral immune response to a different antigen. By administering a lipopeptide of the.present invention to a patient in combination with a different specific antigen, the patient's immune response to the antigen may be enhanced. In this aspect, the lipopeptide may be administered within the same preparation (e.g., vaccine) as the antigen, or may be administered separately. In general, however, the antigen and the lipopeptide are administered at the same time and site. In this manner, a lipopeptide may be used, for example, as an adjuvant in vaccine preparations for heterologous agents. In another manner, the lipopeptide is both the adjuvant and the antigen in one agent. Suitable doses and methods of administration are presented in detail below.

A lipopeptide of the present invention may be administered to tuberculosis-infected individuals to stimulate. the production of interleukin-12 and of the type 1/Th1 T cell response. Administration of a lipopeptide of the present invention to fresh human monocytes has been found to result in a production of IL-12. The lipopeptides of the present invention may be administered, for example, to patients suffering from an intracellular pathogen-related disease or from a γ-interferon-sensitive tumor to stimulate a curative immune response.

In yet another ermbodiment of the present invention, a lipopeptide may be administered to a patient afflicted with a disease responsive to interleukin-12 stimulation. Such diseases include infections, or diseases such as cancer. In general, the responsiveness of a particular disease to IL-12 stimulation may be determined by evaluating the effect of treatment with a lipopeptide of the present invention on clinical correlates of immunity. For example, if treatment results in a heightened type 1/Th1 T cell response or the conversion of a type 2/Th2 response to a type 1/Th1 T cell profile, with accompanying clinical improvement in the treated patient, the disease is responsive to IL-12 stimulation. Lipopeptide administration may be as described below, or may extend for a longer period of time, depending on the indication.

In the above embodiments, in which a lipopeptide of the present invention is used to stimulate or enhance an immune response in a patient, the lipopeptide is preferably formulated as a pharmaceutical composition or a vaccine. A pharmaceutical composition or a vaccine generally comprises a lipopeptide in combination with a physiologically acceptable carrier, excipient or diluent. Such carriers will be nontoxic to recipients at the dosages and concentrations employed.

Routes of administration, frequency of administration, and doses will vary from individual to individual and may parallel those currently being used in immunization or treatment of other infections. In general, the pharmaceutical compositions and vaccines may be administered by injection (e.g., intramuscular, intravenous or subcutaneous), intranasally (e.g., by aspiration) or orally. The amount and frequency of administration will depend, of course, on such factors as the nature and severity of the indication being treated, the desired response, the condition of the patient, and the like. Typically, between 1 and 4 doses may be administered for a 2–6 week period. Preferably, two doses are administered, with the second dose 2–4 weeks later than the first. A suitable dose is an amount of lipopeptide that stimulates the production of IL-12 in the patient, such that the amount of IL-12 in supernatants of PBMCs isolated from the patient is between about 10 ng and 10:g per mL. In general, the amount of IL-12 may be determined using any appropriate assay known to those of ordinary skill in the art, including the assays described herein. The amount of lipopeptide present in a dose typically ranges from about 1 pg to about 100 mg per kg of host, preferably from about 10 pg to about 1 mg and more preferably, from about 100 pg to about 1:g. Suitable dose sizes will vary with the size of the subject, but will typically range from about 0.01 mL to about 5 mL for 10–60 kg subject. Specific appropriate dosages for a particular indication can be readily determined.

While any suitable carrier known to those of ordinary skill in the art may be employed in the pharmaceutical compositions of this invention, the type of carrier will vary depending on the mode of administration and whether a sustained release administration is desired. For parenteral administration, such as subcutaneous injection, the carrier preferably comprises water, saline, alcohol, a fat, a wax or a buffer. For oral administration, any of the above carriers or a solid carrier, such as mannitol; lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention.

Pharmaceutical compositions and vaccines may also contain diluents such as buffers, antioxidants such as ascorbic acid, low molecular weight (less than about 10 residues) polypeptides, proteins, arnino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, product is formulated as a lyophilizate using appropriate excipient solutions (e.g., sucrose) as diluents.

Any of a variety of adjuvants may be employed in the vaccines or pharmaceutical compositions of this invention, in addition to the lipopeptide, to nonspecifically enhance the immune response. Most adjuvants contain a substance designed to protect the antigen trom rapid catabolism, such as aluminum hydroxide or mineral oil, and a nonspecific stimulator of immune responses, such as lipid A, or *Bordella pertussis.*

The ability of a lipopeptide to stimulate interleukin-12 production correlates with the development of a protective, type 1/Th1 T cell response in normal people, in infected patients, in PBMCs from normal people, and in PBMCs isolated from infected patients. Therefore, determining whether a selected lipopeptide is capable of stimulating IL-12 production provides a rapid, reproducible screening method for use in vaccine development. Lipopeptides capable of eliciting a type 1/Th1 response, as demonstrated by the stimulation of IL-12 production in normal peripheral blood mononuclear cells using the above-described methods, are generally suitable for preparation of a vaccine.

For derivatives in which a lipopeptide is joined to another peptide, a fusion protein may be prepared using recombinant DNA. In one embodiment, the lipopeptide may be conjugated to a signal or leader peptide sequence at the N-terminal region of the protein which post-translationally is modified to the lipopeptide form in an acyltransferase-containing host.

Protein fusions within the present invention may also comprise peptides added to facilitate purification or identification of a lipopeptide. Further, fusion proteins capped with such peptides may be resistant to intracellular degradation in a recombinant host.

Peripheral blood mononuclear cells refer to preparations of nuclear cells present in peripheral blood. Monocytes are large mononuclear cells that constitute three to eight percent of the peripheral blood leukocytes. Their cytoplasm is much more abundant than that of the lymphocytes. Lysosomes filled with degradative enzymes appear as small vacuoles in the cytoplasm. Monocytes originate from promonocytes, which are rapidly dividing precursors in the bone marrow. When the mature cells enter the peripheral blood, they are called monocytes; when they leave the blood and infiltrate tissues, they undergo additional changes and are then known as macrophages. PBMCs may be isolated by methods known to those in the art, density centrifugation through, for example, FicollJ (Winthrop Laboratories, New York).

Table 1 lists the identity of sequences of the present disclosure having sequence identifiers.

TABLE 1

Identification of Sequences Having Sequence Identifiers

| SEQ ID NO: | IDENTITY |
|---|---|
| 1 | Deduced amino acid sequence of the 19 kDa antigen of *M. tuberculosis* (from Ashbridge et al., Nucleic Acids Research 17(3):1249) |
| 2 | Amino acid sequence of the mature 19 kDa antigen without the N-terminal signal peptide, Xaa indicates a lipid-derivatized cysteine residue |
| 3 | Amino acid sequence of an N-terminal hexapeptide of the mature 19 kDa antigen, Xaa-Ser-Ser-Asn-Lys-Ser; Xaa indicates a lipid-derivatized cysteine residue |
| 4 | Nucleotide sequence of the putative gene for the *M. tuberculosis* 19 kDa antigen (from Ashbridge, ibid.) |
| 5 | Deduced amino acid sequence of the 38 kDa antigen of *M. tuberculosis* (from Andersen and Hansen, Infection and Immunity 57(8):2481, 1989) |
| 6 | Amino acid sequence of a postulated mature 38 kDa antigen without an N-terminal signal peptide, Xaa indicates a lipid-derivatized cysteine residue |
| 7 | Amino acid sequence of an N-terminal hexapeptide of a mature 38 kDa antigen, Xaa-Gly-Ser-Lys-Pro-Pro; Xaa indicates a lipid-derivatized cysteine residue |
| 8 | Xaa-Ser-Ser-Asn-Ala |
| 9 | Xaa-Gly-Ser-Ser-His-His |
| 10 | Xaa-Ser-Ser-Lys-Thr-Asp |
| 11 | Xaa-Lys-Gln-Asn-Val-Ser- |

TABLE 1-continued

Identification of Sequences Having Sequence Identifiers

| SEQ ID NO: | IDENTITY |
|---|---|
| 12 | Xaa-Ala-Gln-Lys-Gly-Ala |
| 13 | Xaa-Ala-Gly |
| 14 | Xaa-Ser |

The following methods were followed in the studies provided as examples herein, and are not meant to be limiting.

Cell preparations. The human monocytic cell line, THP-1, was used as a source of homogenous monocytes in the majority of the studies. The THP-1 cell line used was kindly provided by Dr. R. Ulevitch (Scripps Research Institute, La Jolla, Calif.) and had been stably transfected with an unmodified pRc/RSV vector (Invitrogen, Inc.). This variant of the THP-1 cell line was used specifically because it expressed low levels of CD14 and did not produce IL-12 p40 in response to LPS at concentrations as high as 25 endotoxin units/ml. The cell line was maintained in RPMI 1640 medium supplemented with 10% heat-inactivated fetal bovine serum at 37EC in a 5% $CO_2$ incubator.

Preparation of peripheral blood mononuclear cells: Peripheral blood from healthy, tuberculin-negative, donors was collected in heparinized tubes. Peripheral blood mononuclear cells (PBMC) were isolated on Ficoll-hypaque gradients (Pharmacia LKB Biotechnology Inc., Piscataway N.J.).

*M. tuberculosis* subcellular fractions. *Mycobacterium tuberculosis* H37rv (Patrick Brennan and John Belisle) was γ-irradiated and prepared by probe sonication. Various subcellular fractions were isolated by standard procedures. The level of lipopolysaccharide in the fractions was measured quantitatively with a Limulus Amoebocyte Lysate assay (Whittaker Bioproducts, Walkersville Md.).

Collection of cell culture supernatants. THP-1 cells were plated at a concentration of $2 \times 10^5$ cells/well in 96-well plates. The cells were cultured in the presence of various *M. tuberculcsis* preparations. at 37EC in a $CO_2$ incubator with RPMI 1640 and 10% heat-inactivated fetal bovine serum. Cell-free supematants were harvested 20 hours later and stored at −20EC until assayed for cytokine levels by ELISA. All samples were assayed in duplicate.

ELJSA for IL-12 p40. 96-well ELISA plates (Coming Glass Works, Coming, N.Y.) were coated overnight at 4EC with 100:1 of rat anti-human IL-12 mAb (2.5:g/ml, mAb 2–4A1 (specific for p40); a gift from Dr. Maurice Gately, Hoffmran-La Roche Inc., Nutley, N.J.). Plates were incubated with 150:1 of 1% BSA (Fisher Biotech, Pittsburgh, Pa.) in PBS for 1 h at room temperature. 100:1 aliquots of each sample were then added to each well. Samples were were incubated with 150:1 of 1% BSA (Fisher Biotech, Pittsburgh, PA) in PBS for 1 heat room temperature. 100:1 aliquots of each sample were then added to each well. Samples were incubated at room temperature for 2 h, and standard dilutions for IL-12 p40. Reagents for the IL-12 p40 ELISA were provided by Dr. Maurice Gately, Hoffinan-La Roche, Inc. were also evaluated. Peroxidase-conjugated anti-IL-12 mAb (POD-4D6, 179 ng/ml; Dr. Maurice Gately), was added to each well and incubated for 1 h. Peroxidase substrate solution (Krkegaard & Perry Laboratories Inc., Gaithersburg, Md.) was used to detect IL-12 p40. Plates were read in an ELISA reader (Biotech Instruments, Luton, UK) at a wavelength of 405 nm.

Characterization of anti-mouse IL-12 monoclonal antibodies and measurement of mouse IL-12 by an ELISA was conducted as described in *J. Immunol. Methods*, 189(1):15–24 (1996). The lipoprotein, manLAM, was provided by John Belisle, and is described in Berman, et al., *J. Immunol.* 156(10):3828–35 (1996).

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

IL-12-Inducing Capacity of *M. tuberculosis* Subcellular Fractions

The present example demonstrates the IL-12-inducing capacity of *M. tuberculosis* subcellular fractions. *M. tuberculosis* H37rv was γ-irradiated, lysed, and fractionated using standard procedures as shown in the following flow diagram.

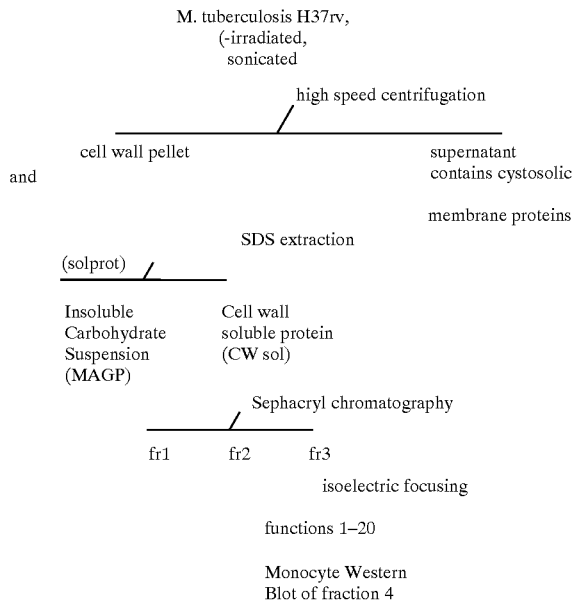

To determine which subcellular fractions induced IL-12 release from monocytes, a variant of the THP-1 cell line was used that expresses low levels of CD14, and therefore does not respond to LPS at concentrations below 25 endotoxin units/ml. The low CD14 expressing characteristics of this THP-1 cell line variant does not appear to be due to transfection with the pRc/RSV vector. THP-1 cells were incubated for 20 h with whole lysate and separately with *M. tuberculosis* fractions, the incubates were centrifuged, resulting supernatants were collected, and IL-12 p40 concentrations in the supernatants Were determined by ELISA. As compared to lysed *M. tuberculosis*, the cell wall-associated fraction (SCWP) contained the majority of the IL-12 p40-inducing capacity as shown in FIG. 1. The cytosolic fraction (solprot) was less potent on a weight basis, and the mycobacterial lipoglycan from *M. tuberculosis* (manLAM) was unable to induce any IL-12 p40 production up to a final concentration of 10 μg/ml (FIG. 1).

EXAMPLE 2

Detergent-Soluble Cell Wall Proteins Induce IL-12 Production

Figure 2:
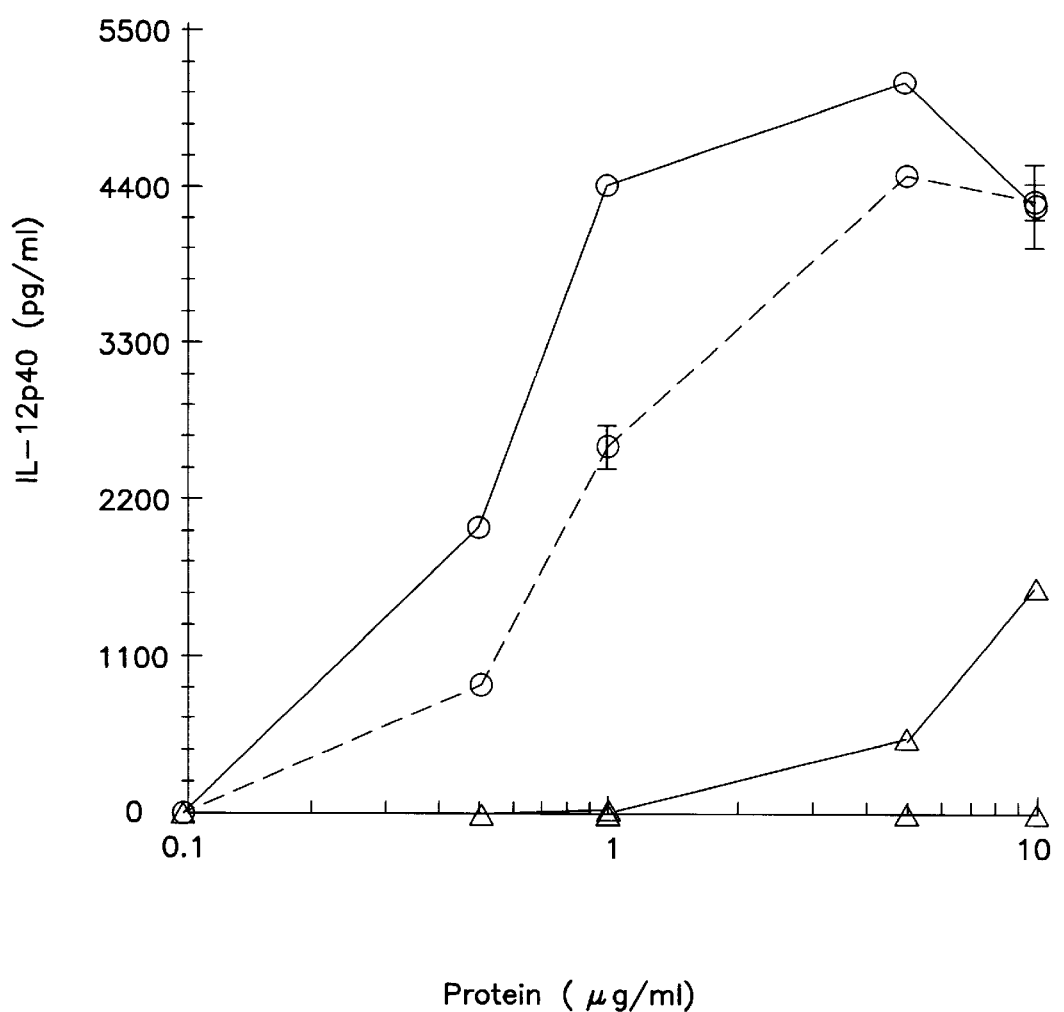
FIG. 2. The detergent-soluble proteins of the cell wall induce IL-12 p40 production, and their effect is not due to phagocytosis of protein-adsorbed particulate matter as described in Example 2. Values are expressedlas mean±SEM of duplicate determinations. Symbols: ○ SCWP (detergent soluble cell wall fraction); A MAGP (detergent insoluble cell wall fraction); solid line—unfiltered antigen preparation, dashed line—filtered antigen preparation through 0.2 μm filter.

The present example provides data showing that detergent-soluble cell wall proteins induce IL-12 production. The cell wall pellet fraction was extracted with SDS detergent and centrifuged to generate a protein-rich cell wall soluble fraction (SCWP) and an insoluble, carbohydrate-rich suspension termed MAGP. THP-1 cells were stimulated with the soluble, protein-rich, cell wall fraction (SCWP) and the insoluble, carbohydrate-rich, cell wall suspension (MAGP) in a dose-dependent fashion from 0.1 to 10: g/ml. Cell-free supernatants were collected at 20 h and assayed for IL-12 p40 by ELISA. Each fraction was assayed for IL-12 p40. Again, most of the IL-12 p40-inducing activity was in the SCWP fraction compared to the MAGP fraction at each concentration of the stimulus as shown in FIG. 2. Since macrophage phagocytosis of protein-adsorbed particulate suspensions had been reported to induce IL-12 release, the SCWP and the MAGP fractions were filtered through a 0.2 mm sterile filter, and the assay for IL-12 p40 was repeated on the filtered fractions. The SCWP fraction retained the majority of its IL-12 p40-inducing activity after filtration; whereas the MAGP suspension lost all of its activity over the entire range of concentrations (FIG. 2). In addition, SDS alone in concentrations present in the SCWP fraction did not result in any IL-12 p40 release. These data indicate that the IL-12 p40-inducing capacity of the *M. tuberculosis* cell wall resides primarily in the detergent soluble, protein-rich fraction, and that the majority of the IL-12 p40-inducing activity is not dependent upon phagocytosis of insoluble particles.

EXAMPLE 3

Figure 3:
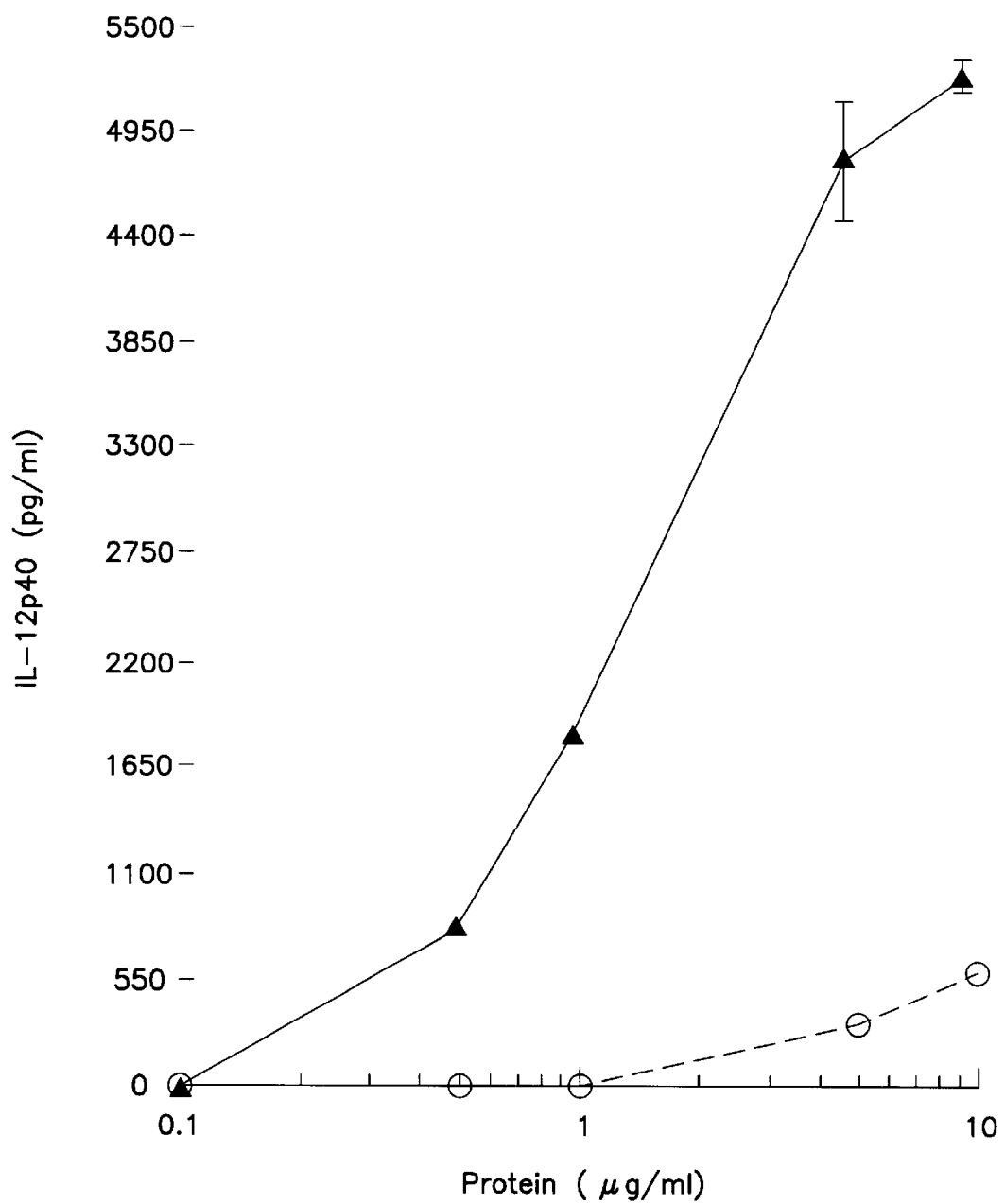
FIG. 3. The culture filtrate proteins of *M. tuberculosis* (○) are not significant stimulators of IL-12 p40 production compared to the cell wall-associated proteins, SCWP (▼). Values are expressed as mean±SEM of duplicate determinations.

Secreted Proteins of *M. tuberculosis* do not Play a Major Role in IL-12 Induction The present example provides a comparison of IL-12-inducing capacity of cell wall-associated proteins versus culture-filtrate proteins. The culture filtrate of *M. tuberculosis* contains a collection of immunogenic proteins that may be important in the development of T-cell mediated immunity. Therefore, the IL-12 p40-inducing capacity of *M. tuberculosis* H37rv culture filtrate was compared with the cell wall-associated protein fraction (SCWP). THP-1 cells were stimulated with cell wall-associated proteins (SCWP) and culture-filtrate proteins in a dose-dependent fashion from 0.1 to 10 μg/ml. Cell-free supernatants were collected at 20 h and assayed for IL-12 p40 by ELISA. Over the concentration range of 0.1–10 μg/ml, the SCWP fraction proved to be a much more potent inducer of IL-12 p40 production than the culture filtrate (FIG. 3). This result demonstrates that the secreted proteins of *M. tuberculosis* do not play a major role in monocyte/macrophage production of IL-12 following infection, and that cell wall-associated proteins are the predominant stimulus.

EXAMPLE 4

Purification of the IL-12 Inducing Activity

Figure 4:
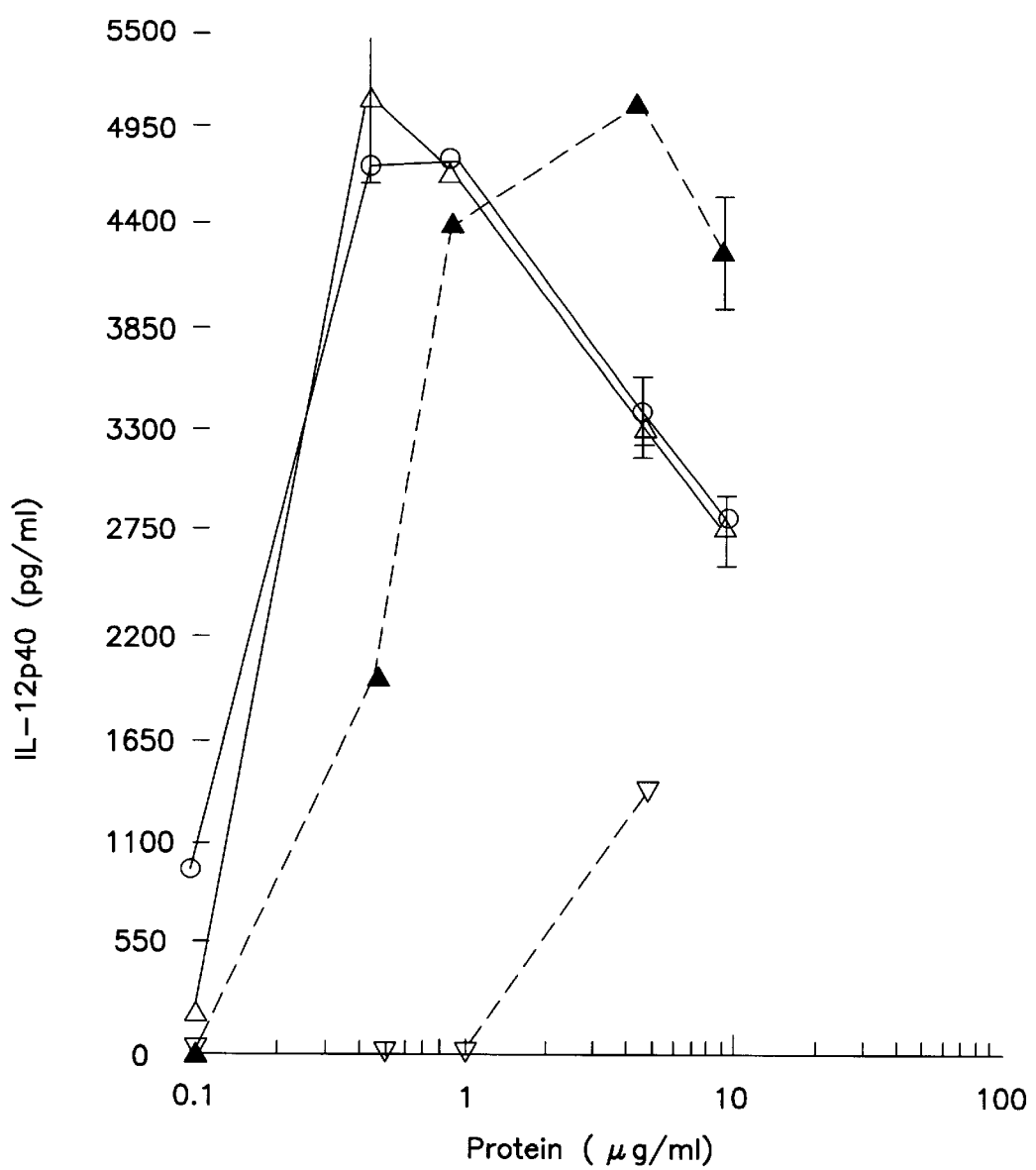
FIG. 4. Purification of IL-12 p40-inducing activity by Sephacryl S-200 size fractionation of the cell wall-associated proteins(SCWP) as described in Example 4. Symbols: □, fraction #1; ○, fraction #2; Δ, fraction #3; ▼, SCWP. Values are expressed as mean±SEM of duplicate determinations.1

The present example provides for the purification of the IL-12-inducing activity from the cell wall-associated protein fraction. To identify the cell wall-associated proteins responsible for IL-12 p40 release, the SCWP preparation was size-fractionated on a Sephacryl column. THP-1 cells were stimulated with Sephacryl fractions #1, 2, and 3 in a dose-dependent fashion from 0.1 to 10 µg/ml. Cell-free supernatants were collected at 20 h and assayed for IL-12 p40 by ELISA. The IL-12 p40-inducing activity was retained predominantly in fractions #2 and #3, with weak activity in fraction #1 (FIG. 4). In comparison to the initial SCWP preparation (FIG. 4), the dose-response curves of Sephacryl fractions #2 and #3 are shifted to the left indicating enrichment of the IL-12 p40-inducing components in those fractions.

Figure 5:
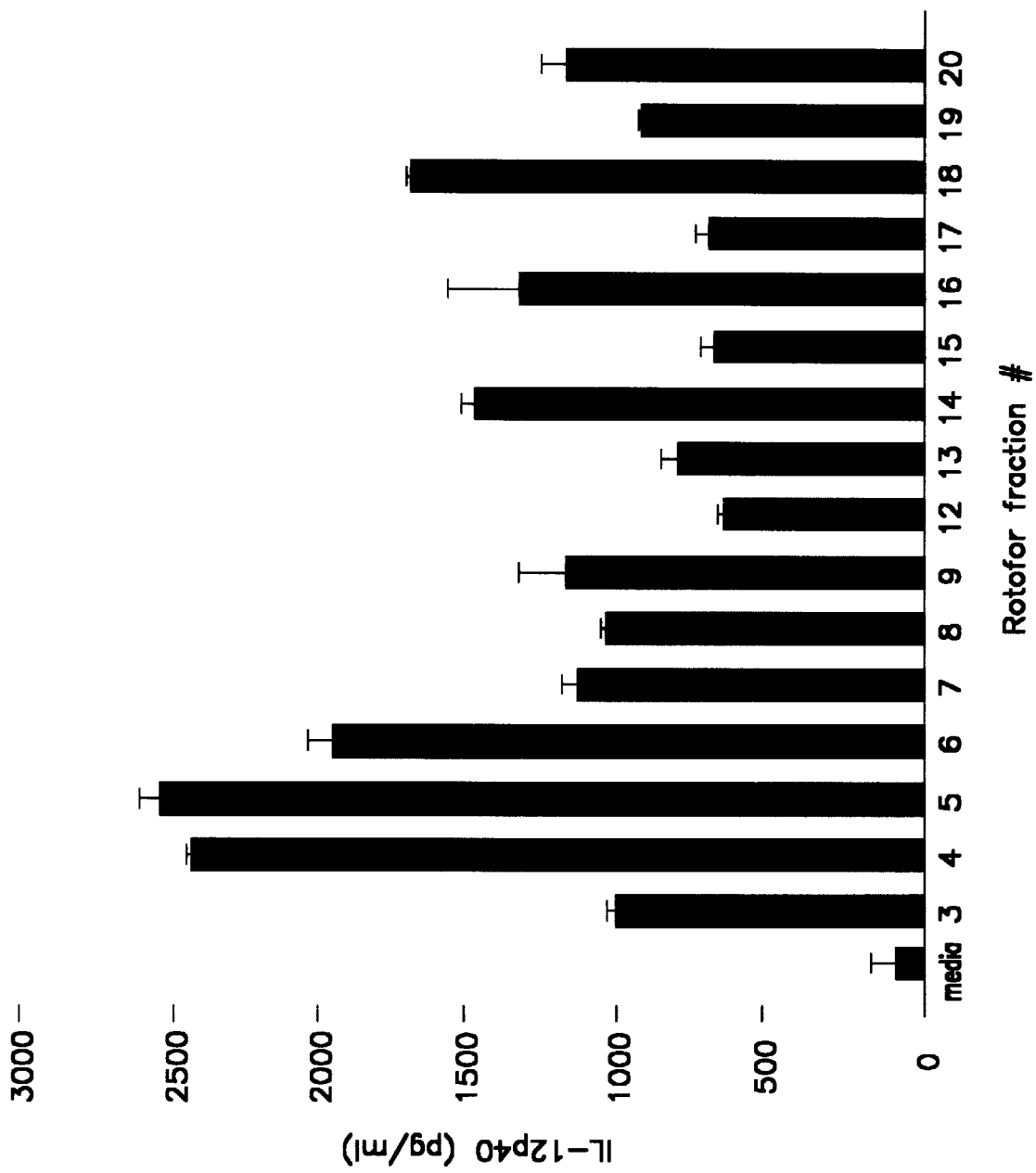
FIG. 5. Purification of the IL-12 p40-inducing activity by preparative isoelectric focusing (Rotofor column) of Sephacryl fraction #3 as described in Example 4. Values are expressed as mean±SEM of duplicate determinations.
Figure 6:
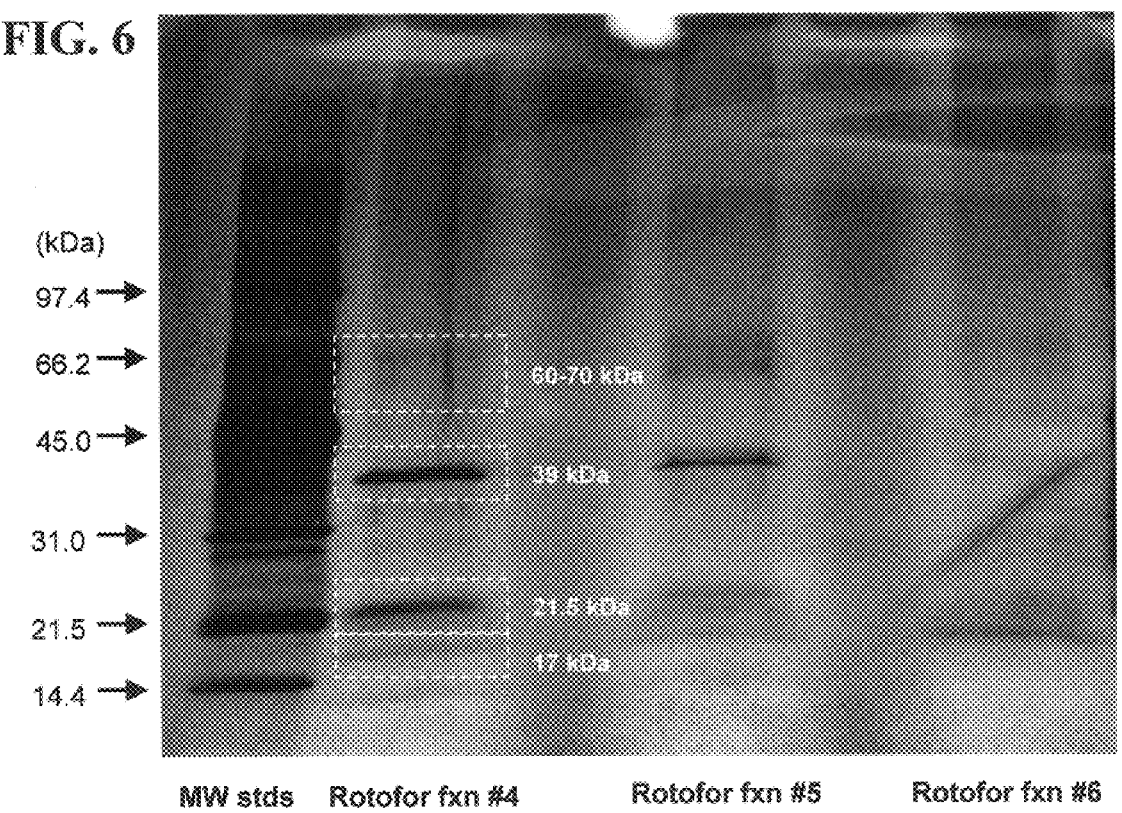
FIG. 6. Polyacrylamide gel electrophoresis of Rotofor fraction #4 under denaturing conditions. Total protein was visualized by silver staining and revealed four prominently stained bands at 17 kDa, 21.5 kDa, 39 kDa, and a doublet at 60–70 kDa.

Sephacryl fraction #3 was further separated by preparative isoelectric focusing on a Rotofor column. Twenty fractions were collected, of which eighteen were demonstrated to have protein by silver staining of a Tris-glycine gel. THP-1 cells were stimulated with Rotofor fractions 3–9, and 12–20 at a concentration of 625 ng/ml. (Fractions 1,2 resulted in cell death at this concentration, and fractions 10,11 did not contain protein). Cell-free supernatants were collected at 20 h and assayed for IL-12 p40 by ELISA. At a protein concentration of 625 ng/ml, fractions 4, 5, and 6 induced the highest levels of IL-12 p40 release (FIG. 5).

Figure 7:
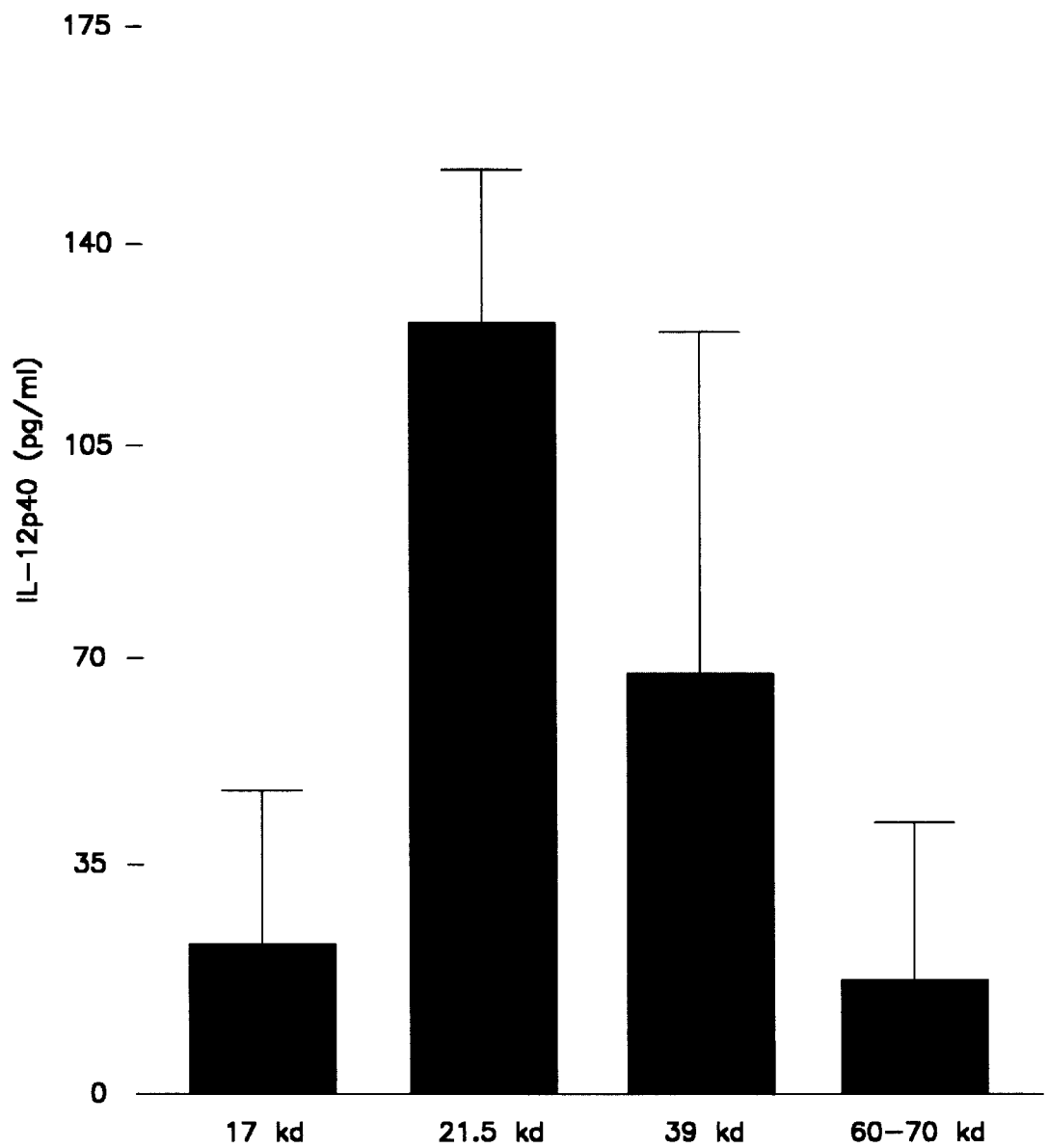
FIG. 7. Monocyte Western blot of Rotofor fraction #4 reveals that the band migrating to 21.5 kDa induces the highest levels of IL-12 p40 as described in Example 4. The mean±SEM of four such studies is presented.

Subsequent separation of the proteins in Rotofor fraction 4 was performed usingsa 4–20% gradient denaturing Tris-glycine gel. Total protein was visualized by silver staining. Four stained proteins were identified as migrating to 17 kDa, 21.5 kDa, 39 kDa, and a doublet at 60–70 kDa. Following transfer to nitrocellulose, these four regions of the Tris-glycine gel derived from Rotofor fraction #4 were solubilized and used to stimulate THP-1 cells. The average of results from four such experiments is summarized in FIG. 7. The band migrating to 21.5 kDa induced the highest levels of IL-12 p40 release; followed by the 39 kDa band, with the two other regions inducing little activity. By using monoclonal antibodies to known *M. tuberculosis* antigens in a Western blot of the same fraction, the 21.5 kDa band was identified as the 19 kDa lipoprotein antigen of *M. tuberculosis* and the 39 kDa band was identified as the *M. tuberculosis* 38 kDa lipoprotein antigen. In summary, these data indicate that the 19 kDa lipoprotein is the major inducer of IL-12 p40 production in THP-1 cells, with some contribution from the 38 kDa lipoprotein.

EXAMPLE 5

The 19 kDa Lipoprotein of *M. tuberculosis* is a Potent Inducer of IL-12 Release In order to further assess their IL-12 p40-inducing capabilities, the 19 kDa and 38 kDa lipoproteins of *M. tuberculosis* H37rv were purified and used to stimulate THP-1 cells in a dose-dependent manner from 1 ng/ml to 10 µg/ml. The 19 kDa and 38 kDa preparations were >99% pure as assessed by SDS-PAGE. Their IL-12 p40-inducing potency was compared to sonicated *M. tuberculosis* and a similarly prepared irrelevant *M. tuberculosis* protein (the antigen 85 complex). Cell-free supernatants were collected at 20 h and assayed for IL-12 p40 by ELISA.

Figure 8:
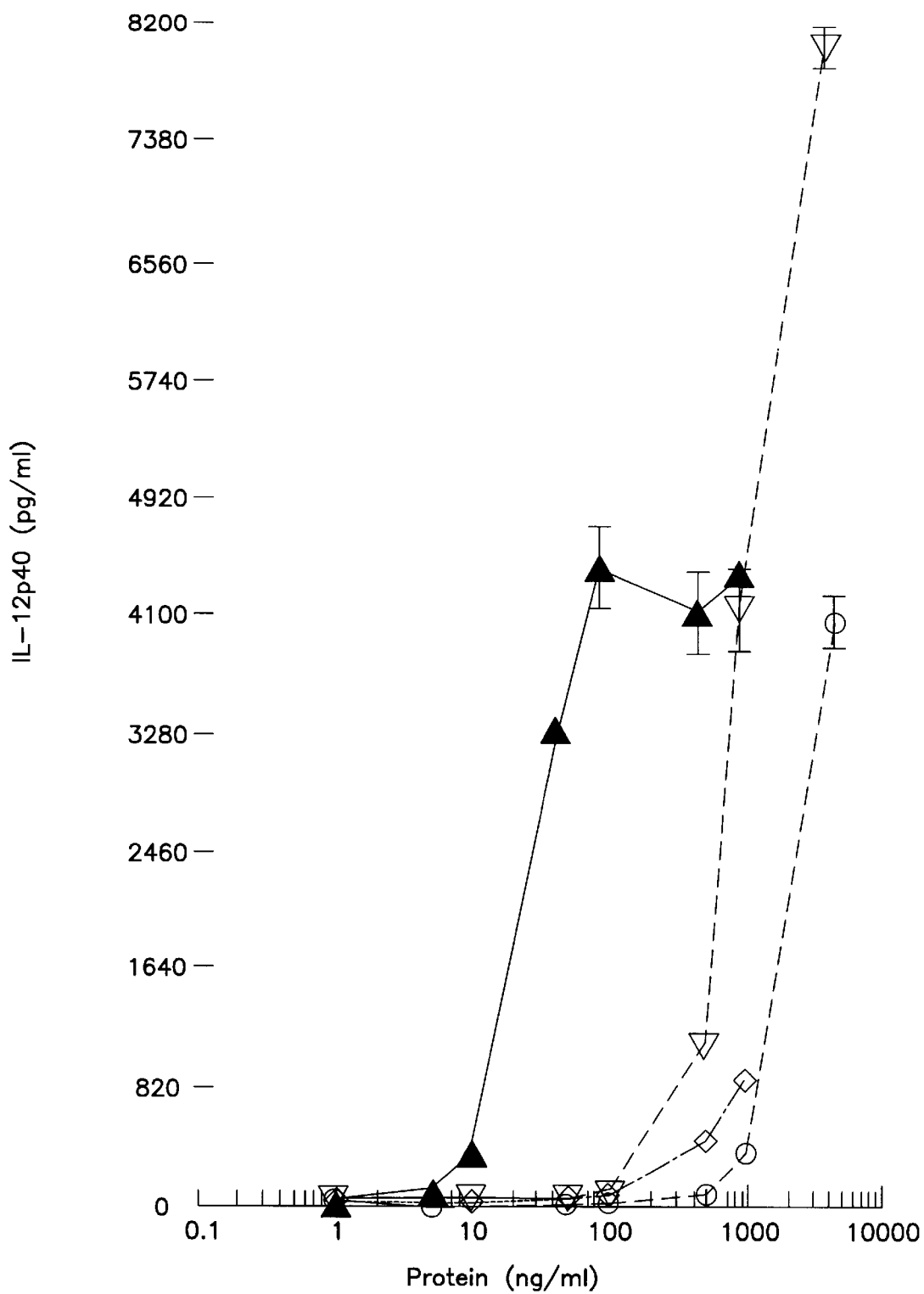
FIG. 8. The 19 kDa lipoprotein of *M. tuberculosis* is a potent inducer of IL-12 p40 release as described in Example 5. Symbols: ▼, 19 kDa; Δ, 38 kDa; ○, Ag85 complex; ◇, M. tb lysate. Values are expressed as mean±SEM of duplicate determinations.

As compared to *M. tuberculosis* sonicate, only the 19 kDa lipoprotein demonstrated a left shift of the dose response curve with a 1–1.5 log increase in IL-12 p40-inducing potency (FIG. 8). As little as 10 ng/ml (0.52 nM) of the 19 kDa antigen produced measurable IL-12 p40. This study demonstrates that the *M. tuberculosis* 19 kDa lipoprotein is the more potent, and likely the more physiologically relevant, inducer of IL-12 p40 production in human monocytic cells.

EXAMPLE 6

Induction of IL-12 in Human Monocytes

The present example provides data that show that the 19 kDa lipoprotein of M. tuberculosis induces IL-12 production in fresh human monocytes. Adherent PBMC from a tuberculin-negative healthy donor was incubated with the 19 kDa antigen at a concentration of 5–50 ng/ml. The LPS content in these assays ranged from 0.125–10 1.25 endotoxin units/ml. In order to address any potential contribution of the LPS, IL-12 p40 production by *M. tuberculosis* 19 kDa and *E. coli* LPS was measured in the presence and absence of a blocking anti-CD14 antibody, My4 (FIGS. 9A, 9B). The effect of LPS in the 19 kDa preparation was completely blocked by the anti-CD14 antibody and did not significantly contribute to the IL-12 p40 inducing capability of the *M. tuberculosis* 19 kDa antigen.

These data indicate that the *M. tuberculosis* 19 kDa lipoprotein is a potent inducer of IL-12 p40 production in freshly isolated peripheral blood human monocytes and acts in a CD-14 independent manner.

Innate immunity pertains to immunologic responses which are preprogrammed, and utilizes pattern recognition molecules to identify macromolecular structures. In particular, monocytes participate in the innate immune response through the ability of the CD14 receptor to recognize the lipid portion of lipoglycans, such as LPS, resulting in the release of cytokines. The present studies were carried out using a THP-1 monocyte variant that weakly expressed CD14 and responded poorly to LPS. Therefore, the 19 kDa protein activates monocytes in a CD14-independent manner.

EXAMPLE 7

The 19 kDa lipoprotein of *M. tuberculosis* requires appropriate post-translational modification in order to retain its IL-12 inducing capacity. The present example demonstrates the utility of the present invention as a method for inducing IL-12 release.

Figure 10:
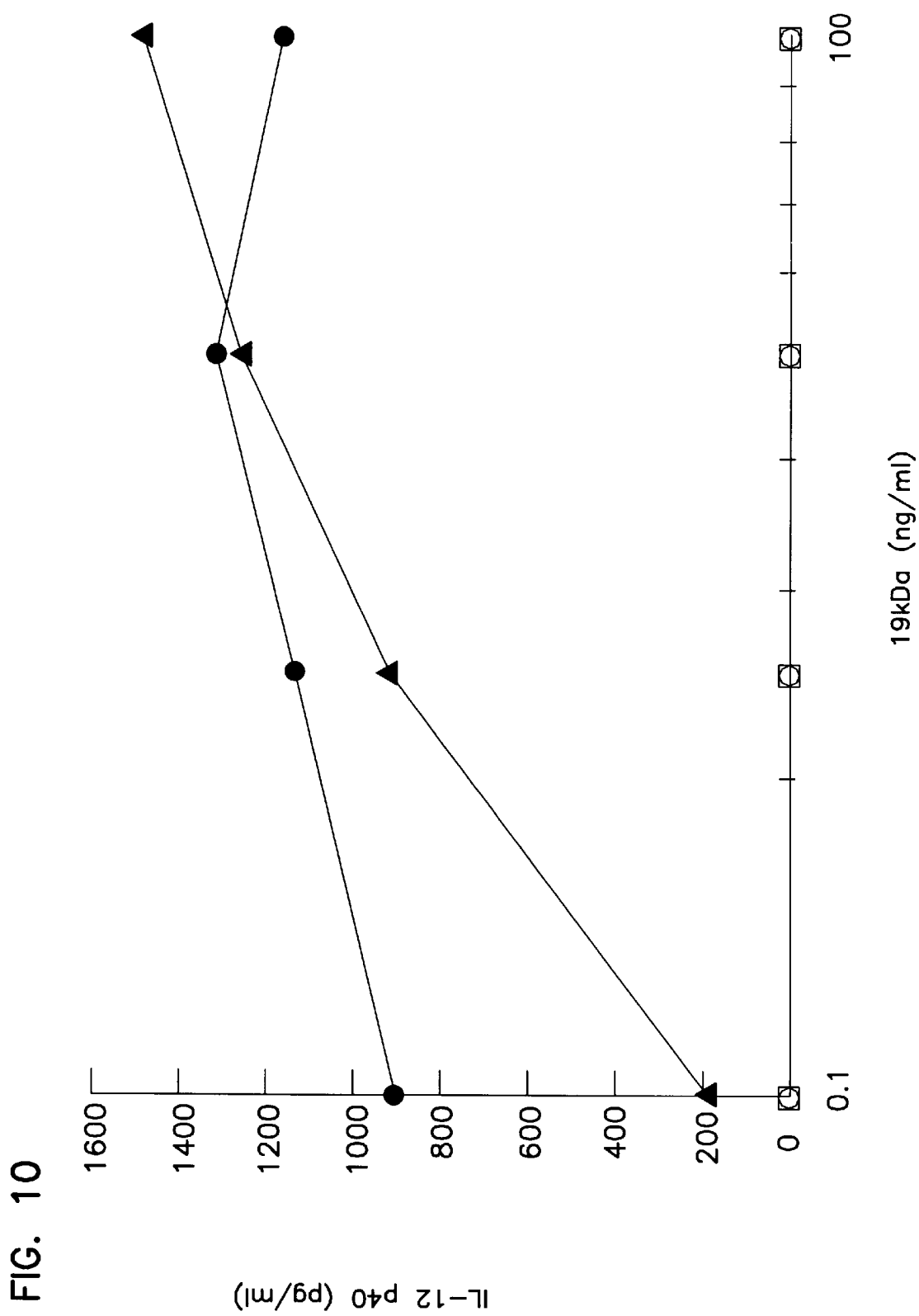
FIG. 10. The 19 kDa lipoprotein of *M. tuberculosis* requires appropriate post-translational modification to stimulate IL-12 p40 production as described in Example 7. Values are expressed as the mean of duplicate determinations. Symbols: 574 , 19 kDa purified from *M. tuberculosis*; ▼ recombinant 19 kDa expressed in *M. vaccae*; ○, recombinant 19 kDa expressed in *E. coli*; □, recombinant, deaclated 19 kDa expressed in *E. coli*.

THP-1 cells were incubated with one of four preparations of the *M. tuberculosis* 19 kDa antigen in a dose-dependent fashion from 10–100 ng/ml. The four preparations were; i) purified *M. tuberculosis* 19 kDa lipoprotein as used in the previous experiments; ii) a recombinant form of the *M. tuberculosis* 19 kDa antigen expressed in a mycobacterial system, *M. vaccae*; iii) a recombinant form of the *M. tuberculosis* 19 kDa antigen expressed in *E. coli*; and, iv) a recombinant form of the *M. tuberculosis* 19 kDa antigen expressed in *E. coli* with a mutation in the N-terminal signal sequence resulting in a deacylated form of the protein. Cell-free supernatants were collected at 20 h and assayed for IL-12 p40 by ELISA. The recombinant forms of the 19 kDa antigen expressed in *E. coli* failed to induce any IL-12 p40 in the THP-1 cells. The purified form of *M. tuberculosis* 19 kDa and the recombinant antigen expressed in a mycobacterial system stimulated IL-12 p40 release in an equivalent manner (FIG. 10). These data demonstrate that proper acylation and/or gylcosylation of the *M. tuberculosis* 19 kDa protein provides for induction of IL-12 release by human monocytic cells.

All of the compositions and methods disclosed and claimed herein can be made and executed without undue experimentation in light of the present disclosure. While the compositions and methods of this invention have been described in terms of preferred embodiments, it will beapparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The references cited herein, to the extent that they provide exemplary procedural or other details supplementary to those set forth herein, are specifically incorporated herein by reference.

What is claimed is:

1. A method of inducing a type 1/Th1 T-cell response in a subject comprising administering to the subject a lipopeptide having an N-terminal ester- or amide-linked fatty acyl group, in an amount effective to induce the type 1/Th1 T-cell response, wherein the lipopeptide is Xaa-Ser-Ser-Asn-Lys-Ser (SEQ ID NO:3), wherein Xaa is an N-acyldiacylglycerolcysteine residue.

2. A method of inducing interleukin-12 in a cell comprising administering to the cell a lipopeptide having an N-terminal ester or amide-linked fatty acyl group in an amount effective to induce interleukin-12 in the cell, wherein the lipopeptide is Xaa-Ser-Ser-Asn-Lys-Ser (SEQ ID NO: 3), wherein Xaa is an N-acyldiacylglycerol cysteine residue.

* * * * *

SEQUENCE LISTING

```
<160> NUMBER OF SEQ ID NOS: 14

<210> SEQ ID NO 1
<211> LENGTH: 159
<212> TYPE: PRT
<213> ORGANISM: Mycobacterium tuberculosis
<300> PUBLICATION INFORMATION:
<303> JOURNAL: Nucleic Acids Res.
<304> VOLUME: 17
<305> ISSUE: 3
<306> PAGES: 1249-

<400> SEQUENCE: 1

Val Lys Arg Gly Leu Thr Val Ala Val Ala Gly Ala Ala Ile Leu Val
 1               5                  10                  15

Ala Gly Leu Ser Gly Cys Ser Ser Asn Lys Ser Thr Thr Gly Ser Gly
                20                  25                  30

Glu Thr Thr Thr Ala Ala Gly Thr Thr Ala Ser Pro Gly Ala Ala Ser
            35                  40                  45

Gly Pro Lys Val Val Ile Asp Gly Lys Asp Gln Asn Val Thr Gly Ser
        50                  55                  60

Val Val Cys Thr Thr Ala Ala Gly Asn Val Asn Ile Ala Ile Gly Gly
 65                  70                  75                  80

Ala Ala Thr Gly Ile Ala Ala Val Leu Thr Asp Gly Asn Pro Pro Glu
                85                  90                  95

Val Lys Ser Val Gly Leu Gly Asn Val Asn Gly Val Thr Leu Gly Tyr
                100                 105                 110

Thr Ser Gly Thr Gly Gln Gly Asn Ala Ser Ala Thr Lys Asp Gly Ser
            115                 120                 125

His Tyr Lys Ile Thr Gly Thr Ala Thr Gly Val Asp Met Ala Asn Pro
        130                 135                 140

Met Ser Pro Val Asn Lys Ser Phe Glu Ile Glu Val Thr Cys Ser
145                 150                 155

<210> SEQ ID NO 2
<211> LENGTH: 138
<212> TYPE: PRT
<213> ORGANISM: Mycobacterium tuberculosis
<220> FEATURE:
<221> NAME/KEY: LIPID
<222> LOCATION: (1)
<223> OTHER INFORMATION: Xaa is  N_ACYL DIGLYCERIDE cysteine

<400> SEQUENCE: 2

Xaa Ser Ser Asn Lys Ser Thr Thr Gly Ser Gly Glu Thr Thr Thr Ala
 1               5                  10                  15

Ala Gly Thr Thr Ala Ser Pro Gly Ala Ala Ser Gly Pro Lys Val Val
```

```
                20                  25                  30
Ile Asp Gly Lys Asp Gln Asn Val Thr Gly Ser Val Val Cys Thr Thr
             35                  40                  45

Ala Ala Gly Asn Val Asn Ile Ala Ile Gly Gly Ala Ala Thr Gly Ile
         50                  55                  60

Ala Ala Val Leu Thr Asp Gly Asn Pro Pro Glu Val Lys Ser Val Gly
     65                  70                  75                  80

Leu Gly Asn Val Asn Gly Val Thr Leu Gly Tyr Thr Ser Gly Thr Gly
                 85                  90                  95

Gln Gly Asn Ala Ser Ala Thr Lys Asp Gly Ser His Tyr Lys Ile Thr
            100                 105                 110

Gly Thr Ala Thr Gly Val Asp Met Ala Asn Pro Met Ser Pro Val Asn
        115                 120                 125

Lys Ser Phe Glu Ile Glu Val Thr Cys Ser
    130                 135

<210> SEQ ID NO 3
<211> LENGTH: 6
<212> TYPE: PRT
<213> ORGANISM: Mycobacterium tuberculosis
<220> FEATURE:
<221> NAME/KEY: LIPID
<222> LOCATION: (1)
<223> OTHER INFORMATION: Xaa is  N_ACYL DIGLYCERIDE cysteine

<400> SEQUENCE: 3

Xaa Ser Ser Asn Lys Ser
  1               5

<210> SEQ ID NO 4
<211> LENGTH: 493
<212> TYPE: DNA
<213> ORGANISM: Mycobacterium tuberculosis
<300> PUBLICATION INFORMATION:
<303> JOURNAL: Nucleic Acids Res.
<304> VOLUME: 17
<305> ISSUE: 3
<306> PAGES: 1249-

<400> SEQUENCE: 4
aaaggagcac agggtgaagc gtggactgac ggtcgcggta gccggagccg ccattctggt      60
cgcaggtctt tccggatgtt caagcaacaa gtcgactaca ggaagcggtg agaccacgac     120
cgcggcaggc acgacggcaa gccccggcgc cgcctccggg ccgaaggtcg tcatcgacgg     180
taaggaccag aacgtcaccg gctccgtggt gtgcacaacc gcggccggca atgtcaacat     240
cgcgatcggc ggggcggcga ccggcattgc cgccgtgctc accgacggca accctccgga     300
ggtgaagtcc gttgggctcg gtaacgtcaa cggcgtcacg ctgggataca cgtcgggcac     360
cggacagggt aacgcctcgg caaccaagga cggcagccac tacaagatca ctgggaccgc     420
taccggggtc gacatggcca acccgatgtc accggtgaac aagtcgttcg aaatcgaggt     480
gacctgttcc taa                                                        493

<210> SEQ ID NO 5
<211> LENGTH: 373
<212> TYPE: PRT
<213> ORGANISM: Mycobacterium tuberculosis
<300> PUBLICATION INFORMATION:
<303> JOURNAL: Infect. Immun.
<304> VOLUME: 57
<305> ISSUE: 8
<306> PAGES: 2481-
```

-continued

<307> DATE: 1989

<400> SEQUENCE: 5

```
Met Lys Ile Arg Leu His Thr Leu Leu Ala Val Leu Thr Ala Pro Leu
  1               5                  10                  15

Leu Leu Ala Ala Ala Gly Cys Gly Ser Lys Pro Pro Ser Gly Ser Pro
             20                  25                  30

Glu Thr Gly Ala Gly Ala Gly Thr Val Ala Thr Thr Pro Ala Ser Ser
             35                  40                  45

Pro Val Thr Leu Ala Glu Thr Gly Ser Thr Leu Leu Tyr Pro Leu Phe
         50                  55                  60

Asn Leu Trp Gly Pro Ala Phe His Glu Arg Tyr Pro Asn Val Thr Ile
 65                  70                  75                  80

Thr Ala Gln Gly Thr Gly Ser Gly Ala Gly Ile Ala Gln Ala Ala Ala
                 85                  90                  95

Gly Thr Val Asn Ile Gly Ala Ser Asp Ala Tyr Leu Ser Glu Gly Asp
                100                 105                 110

Met Ala Ala His Lys Gly Leu Met Asn Ile Ala Leu Ala Ile Ser Ala
                115                 120                 125

Gln Gln Val Asn Tyr Asn Leu Pro Gly Val Ser Glu His Leu Lys Leu
130                 135                 140

Asn Gly Lys Val Leu Ala Ala Met Tyr Gln Gly Thr Ile Lys Thr Trp
145                 150                 155                 160

Asp Asp Pro Gln Ile Ala Ala Leu Asn Pro Gly Val Asn Leu Pro Gly
                165                 170                 175

Thr Ala Val Val Pro Leu His Arg Ser Asp Gly Ser Gly Asp Thr Phe
                180                 185                 190

Leu Phe Thr Gln Tyr Leu Ser Lys Gln Asp Pro Glu Gly Trp Gly Lys
                195                 200                 205

Ser Pro Gly Phe Gly Thr Thr Val Asp Phe Pro Ala Val Pro Gly Ala
                210                 215                 220

Leu Gly Glu Asn Gly Asn Gly Gly Met Val Thr Gly Cys Ala Glu Thr
225                 230                 235                 240

Pro Gly Cys Val Ala Tyr Ile Gly Ile Ser Phe Leu Asp Gln Ala Ser
                245                 250                 255

Gln Arg Gly Leu Gly Glu Ala Gln Leu Gly Asn Ser Ser Gly Asn Phe
                260                 265                 270

Leu Leu Pro Asp Ala Gln Ser Ile Gln Ala Ala Ala Gly Phe Ala
                275                 280                 285

Ser Lys Thr Pro Ala Asn Gln Ala Ile Ser Met Ile Asp Gly Pro Ala
290                 295                 300

Pro Asp Gly Tyr Pro Ile Ile Asn Tyr Glu Tyr Ala Ile Val Asn Asn
305                 310                 315                 320

Arg Gln Lys Asp Ala Ala Thr Ala Gln Thr Leu Gln Ala Phe Leu His
                325                 330                 335

Trp Ala Ile Thr Asp Gly Asn Lys Ala Ser Phe Leu Asp Gln Val His
                340                 345                 350

Phe Gln Pro Leu Pro Pro Ala Val Val Lys Leu Ser Asp Ala Leu Ile
                355                 360                 365

Ala Thr Ile Ser Ser
            370
```

<210> SEQ ID NO 6
<211> LENGTH: 351

-continued

<212> TYPE: PRT
<213> ORGANISM: Mycobacterium tuberculosis
<220> FEATURE:
<221> NAME/KEY: LIPID
<222> LOCATION: (1)
<223> OTHER INFORMATION: Xaa is N_ACYL DIGLYCERIDE cysteine

<400> SEQUENCE: 6

```
Xaa Gly Ser Lys Pro Pro Ser Gly Ser Pro Glu Thr Gly Ala Gly Ala
  1               5                  10                  15

Gly Thr Val Ala Thr Thr Pro Ala Ser Ser Pro Val Thr Leu Ala Glu
             20                  25                  30

Thr Gly Ser Thr Leu Leu Tyr Pro Leu Phe Asn Leu Trp Gly Pro Ala
         35                  40                  45

Phe His Glu Arg Tyr Pro Asn Val Thr Ile Thr Ala Gln Gly Thr Gly
     50                  55                  60

Ser Gly Ala Gly Ile Ala Gln Ala Ala Ala Gly Thr Val Asn Ile Gly
 65                  70                  75                  80

Ala Ser Asp Ala Tyr Leu Ser Glu Gly Asp Met Ala Ala His Lys Gly
                 85                  90                  95

Leu Met Asn Ile Ala Leu Ala Ile Ser Ala Gln Gln Val Asn Tyr Asn
            100                 105                 110

Leu Pro Gly Val Ser Glu His Leu Lys Leu Asn Gly Lys Val Leu Ala
        115                 120                 125

Ala Met Tyr Gln Gly Thr Ile Lys Thr Trp Asp Asp Pro Gln Ile Ala
    130                 135                 140

Ala Leu Asn Pro Gly Val Asn Leu Pro Gly Thr Ala Val Val Pro Leu
145                 150                 155                 160

His Arg Ser Asp Gly Ser Gly Asp Thr Phe Leu Phe Thr Gln Tyr Leu
                165                 170                 175

Ser Lys Gln Asp Pro Glu Gly Trp Gly Lys Ser Pro Gly Phe Gly Thr
            180                 185                 190

Thr Val Asp Phe Pro Ala Val Pro Gly Ala Leu Gly Glu Asn Gly Asn
        195                 200                 205

Gly Gly Met Val Thr Gly Cys Ala Glu Thr Pro Gly Cys Val Ala Tyr
    210                 215                 220

Ile Gly Ile Ser Phe Leu Asp Gln Ala Ser Gln Arg Gly Leu Gly Glu
225                 230                 235                 240

Ala Gln Leu Gly Asn Ser Ser Gly Asn Phe Leu Leu Pro Asp Ala Gln
                245                 250                 255

Ser Ile Gln Ala Ala Ala Ala Gly Phe Ala Ser Lys Thr Pro Ala Asn
            260                 265                 270

Gln Ala Ile Ser Met Ile Asp Gly Pro Ala Pro Asp Gly Tyr Pro Ile
        275                 280                 285

Ile Asn Tyr Glu Tyr Ala Ile Val Asn Asn Arg Gln Lys Asp Ala Ala
    290                 295                 300

Thr Ala Gln Thr Leu Gln Ala Phe Leu His Trp Ala Ile Thr Asp Gly
305                 310                 315                 320

Asn Lys Ala Ser Phe Leu Asp Gln Val His Phe Gln Pro Leu Pro Pro
                325                 330                 335

Ala Val Val Lys Leu Ser Asp Ala Leu Ile Ala Thr Ile Ser Ser
            340                 345                 350
```

<210> SEQ ID NO 7
<211> LENGTH: 6
<212> TYPE: PRT

```
<213> ORGANISM: Mycobacterium tuberculosis
<220> FEATURE:
<221> NAME/KEY: LIPID
<222> LOCATION: (1)
<223> OTHER INFORMATION: Xaa is  N_ACYL DIGLYCERIDE cysteine

<400> SEQUENCE: 7

Xaa Gly Ser Lys Pro Pro
 1               5

<210> SEQ ID NO 8
<211> LENGTH: 5
<212> TYPE: PRT
<213> ORGANISM: Mycobacterium tuberculosis
<220> FEATURE:
<221> NAME/KEY: LIPID
<222> LOCATION: (1)
<223> OTHER INFORMATION: Xaa is N_ACYL DIGLYCERIDE cysteine

<400> SEQUENCE: 8

Xaa Ser Ser Asn Ala
 1               5

<210> SEQ ID NO 9
<211> LENGTH: 6
<212> TYPE: PRT
<213> ORGANISM: Mycobacterium tuberculosis
<220> FEATURE:
<221> NAME/KEY: LIPID
<222> LOCATION: (1)
<223> OTHER INFORMATION: Xaa is N_ACYL DIGLYCERIDE cysteine

<400> SEQUENCE: 9

Xaa Gly Ser Ser His His
 1               5

<210> SEQ ID NO 10
<211> LENGTH: 6
<212> TYPE: PRT
<213> ORGANISM: Mycobacterium tuberculosis
<220> FEATURE:
<221> NAME/KEY: LIPID
<222> LOCATION: (1)
<223> OTHER INFORMATION: Xaa is N_ACYL DIGLYCERIDE cysteine

<400> SEQUENCE: 10

Xaa Ser Ser Lys Thr Asp
 1               5

<210> SEQ ID NO 11
<211> LENGTH: 6
<212> TYPE: PRT
<213> ORGANISM: Mycobacterium tuberculosis
<220> FEATURE:
<221> NAME/KEY: LIPID
<222> LOCATION: (1)
<223> OTHER INFORMATION: Xaa is N_ACYL DIGLYCERIDE cysteine

<400> SEQUENCE: 11

Xaa Lys Gln Asn Val Ser
 1               5

<210> SEQ ID NO 12
<211> LENGTH: 6
<212> TYPE: PRT
<213> ORGANISM: Mycobacterium tuberculosis
<220> FEATURE:
<221> NAME/KEY: LIPID
<222> LOCATION: (1)
```

-continued

```
<223> OTHER INFORMATION: Xaa is N_ACYL DIGLYCERIDE cysteine

<400> SEQUENCE: 12

Xaa Ala Gln Lys Gly Ala
  1               5

<210> SEQ ID NO 13
<211> LENGTH: 3
<212> TYPE: PRT
<213> ORGANISM: Mycobacterium tuberculosis
<220> FEATURE:
<221> NAME/KEY: LIPID
<222> LOCATION: (1)
<223> OTHER INFORMATION: Xaa is N_ACYL DIGLYCERIDE cysteine

<400> SEQUENCE: 13

Xaa Ala Gly
  1

<210> SEQ ID NO 14
<211> LENGTH: 2
<212> TYPE: PRT
<213> ORGANISM: Mycobacterium tuberculosis
<220> FEATURE:
<221> NAME/KEY: LIPID
<222> LOCATION: (1)
<223> OTHER INFORMATION: Xaa is N_ACYL DIGLYCERIDE cysteine

<400> SEQUENCE: 14

Xaa Ser
  1
```